(12) United States Patent
Stepaniants et al.

(10) Patent No.: US 8,600,718 B1
(45) Date of Patent: Dec. 3, 2013

(54) COMPUTER SYSTEMS AND METHODS FOR IDENTIFYING CONSERVED CELLULAR CONSTITUENT CLUSTERS ACROSS DATASETS

(75) Inventors: Serguei Stepaniants, Redmond, WA (US); Pek Y. Lum, Seattle, WA (US); Roy Kuraisa, Seattle, WA (US); Eric E. Schadt, Kirkland, WA (US)

(73) Assignee: Microsoft Corporation, Redmond, WA (US)

( * ) Notice: Subject to any disclaimer, the term of this patent is extended or adjusted under 35 U.S.C. 154(b) by 1511 days.

(21) Appl. No.: 11/985,841

(22) Filed: Nov. 16, 2007

Related U.S. Application Data

(60) Provisional application No. 60/859,723, filed on Nov. 17, 2006.

(51) Int. Cl.
*G06G 7/58* (2006.01)
(52) U.S. Cl.
USPC .......................................................... 703/11
(58) Field of Classification Search
USPC ............................................................ 703/11
See application file for complete search history.

(56) References Cited

PUBLICATIONS

Yap et al. Classification between normal and tumor tissues based on the pair-wise gene expression ratio. BMC Cancer, 2004, vol. 4, article 72, 17 pages.*
Backer, 1995, "Computer-assisted Reasoning in Cluster Analysis," Prentice Hall International (UK) Limited, pp. 161-255.
Brem et al., 2002, "Genetic Dissection of Transcriptional Regulation in Budding Yeast," *Science* 296:752-755.
Cohen et al., 1983, "Applied Multiple Regression/Correlation Analysis for the Behavioral Sciences" Second Edition, Lawrence Erlbaum Associates, Inc., pp. 3-24; 79-132.
Deprimo et al., 2003, "Expression profiling of Blood samples from an SU5416 Phase III metastatic colorectal cancer clinical trial: a novel strategy for biomarker identification," *BMC Cancer* 3:1-12.
Duda et al., 2001, "Pattern Classification," Second Edition, John Wiley & Sons, Inc., pp. 526-530; 551-554; and 568-573.
Eaves et al., 2002, "Combining Mouse Congenic Strains and Microarray Gene Expression Analyses to Study a Complex Trait: The NOD Model of Type 1 Diabetes," *Genome Research* 12:232-243.
Eisen et al., 1998, "Cluster analysis and display of genome-wide expression patterns," Proc. Natl. Acad. Sci. USA, 95, pp. 14863-14868.
Everitt, 1993, "Cluster Analysis", Third Edition, Halsted Press, a Division of John Wiley & Sons, Inc., pp. 55-90 and 125-140.
He et al., 2004, "Citric acid cycle intermediates as ligands for orphan G-protein-coupled receptors," Nature, 429, pp. 188-193.
Hughes et al., 2000, "Functional Discovery via a Compendium of Expression Profiles," *Cell* 102:109-126.
Hyvärinen et al., 2001, "Independent Component Analysis," First Edition, John Wiley & Sons, Inc., pp. 6-10 and 147-164.
Jarvis et al., 1973, "Clustering Using a Similarity Measure Based on Shared Near Neighbors," *IEEE Transactions on Computers* C-22:1025-1034.
Jaspers and Bootsma, 1982, "Genetic heterogeneity in ataxia-telangiectasia studied by cell fusion," *Proc. Natl. Acad. Sci. USA* 79:2641-2644.
Johnson et al., 2003, "Genome-Wide Survey of Human Alternative Pre-mRNA Splicing with Exon Junction Microarrays," *Science* 302:2141-2144.
Jolliffe, 2002, "Principal Component Analysis," Springer-Verlag New York, Inc., Second Edition, pp. 1-61.
Karp et al., 2000, "Identification of complement factor 5 as a susceptibility locus for experimental allergic asthma," *Nature Immunology* 1:221-226.
Kaufman and Rousseeum, 1990, "Finding Groups in Data: An Introduction to Cluster Analysis," John Wiley & Sons, Inc., pp. 1-49.
Kim et al., 2001, "A Gene Expression Map for *Caenorhabditis elegans*," *Science* 293:2087-2092.
Klose et al., 2002, "Genetic analysis of the mouse brain proteome," *Nature Genetics* 30:385-393.
Lance et al., 1967, "A general theory of classificatory sorting strategies," *Computer Journal* 9:373-380.
Lander, 1996, "The New Genomics: Global views of Biology," *Science* 274:536-539.
Schadt et al., 2003, "Genetics of gene expression surveyed in maize, mouse and man," *Nature*, 422:297-302.
Schadt et al., 2003, "A new paradigm for drug discovery: integrating clinical, genetic, genomic and molecular phenotype data to identify drug targets," *Biochemical Society Transactions*, 31: 437-443.
Segal et al., 2003, "Module networks: identifying regulatory modules and their condition-specific regulators from gene expression data," *Nature Genetics* 34:166-176.
Shoemaker et al., 2001, "Experimental annotation of the human genome using microarray technology," *Nature* 09:922-927.
Stuart et al., 2003, "A Gene-Coexpression Network for Global Discovery of Conserved Genetic Modules," *Science* 302:249-255.
Thompson, 1984, "Canonical Correlation Analysis," Sage Publications, Inc., pp. 7-69.
Van De Vijver et al., 2002, "A Gene-Expression Signature as a Predictor of Survival in Breast Cancer," *The New England Journal of Medicine* 347:1999-2009.

(Continued)

*Primary Examiner* — Jerry Lin
(74) *Attorney, Agent, or Firm* — Klarquist Sparkman, LLP

(57) ABSTRACT

Systems and methods for determining a functional relationship between pairs of cellular constituents are provided. A plurality of datasets is received. Each dataset represents an experimental condition and comprises measurement data for a plurality of cellular constituents from each of a plurality of organisms. Each respective dataset is represented by correlation coefficients. Each correlation coefficient for a respective dataset in the plurality of datasets represents a correlation between abundance measurement data for a pair of cellular constituents across the dataset. The plurality of correlation coefficients that represents a first dataset in the plurality of datasets is clustered, thereby determining their order. This order is applied to each remaining dataset thereby forming a plurality of correlation matrices. When a conserved area in the plurality of matrices is identified, the functional relationship between the first cellular constituent and the second constituent is determined to be present.

8 Claims, 15 Drawing Sheets

(56) References Cited

PUBLICATIONS

Van't Veer et al., 2002, "Gene expression profiling predicts clinical outcome of breast cancer," *Nature* 415:530-536.

Waring et al., 2002, "Identifying toxic mechanisms using DNA microarrays: evidence that an experimental inhibitor of cell adhesion molecule expression signals through the aryl hydrocarbon nuclear receptor," *Toxicology*, 181-182:537-550.

Wittenberger et al., 2001, "An Expressed Sequence Tag (EST) Data Mining Strategy Succeeding in the Discovery of New G-Protein Coupled Receptors," *J. Mol. Biol.* 307:799-813.

\* cited by examiner

COMPUTER SYSTEMS AND METHODS FOR IDENTIFYING CONSERVED CELLULAR CONSTITUENT CLUSTERS ACROSS DATASETS

This application claims benefit of U.S. Provisional Patent Application No. 60/859,723, filed on Nov. 17, 2006, which is incorporated herein by reference in its entirety.

1. FIELD OF INVENTION

The field of this invention relates to computer systems and methods for analyzing abundance data of cellular constituents, e.g., gene expression data generated by microarray technology. Computer systems and methods for identifying and analyzing the conserved interactions between pairs of cellular constituents are also disclosed.

2. BACKGROUND OF THE INVENTION

Cellular constituent abundance data from microarrays and, more generally, functional genomics, has become an important tool in life sciences as well as medical research. Cellular constituents are individual genes, proteins, mRNA expressing genes, and/or any other variable cellular component or protein activities such as the degree of protein modification (e.g., phosphorylation), for example, that is typically measured in biological experiments (e.g., by microarray) by those skilled in the art. Significant discoveries relating to the complex networks of biochemical processes underlying living systems, common human diseases, and gene discovery and structure determination can now be attributed to the application of cellular constituent abundance data as part of the research process. See, for example, Hughes et al., 2000, Cell 102, 109; Karp et al., 2000, Nat. Immunol. 1, 221; Schadt et al., 2003, Nature 422, 297; Eaves et al., 2002, Genome Res. 12, 232, and Shoemaker et al., 2001, Nature 409, 922, each of which is hereby incorporated by reference herein in its entirety. Cellular constituent abundance data have also helped to identify biomarkers, discriminate disease subtypes and identify mechanisms of toxicity. See, for example, DePrimo et al., 2003, BMC Cancer 3, 3; van de Vijver et al., 2002, N. Engl. J. Med. 347, 1999; van't Veer et al., 2002, Nature 415, 530; and Waring et al., 2002, Toxicology 181-182, 537, each of which is hereby incorporated by reference herein in its entirety.

The use of cellular constituent abundance data from sources such as microarrays as a tool to identify genes responsible for traits, including common human diseases, continues to prove to be difficult. Elucidating hundreds or even thousands of genes whose expression changes are associated with a disease state does not directly lead to the identification of the key drivers involved in the disease processes. Subsequent validation of candidate genes identified from gene expression experiments is presently a hit-or-miss and time consuming process. This validation typically involves gene knock outs/ins, transgenic construction, siRNA studies, drug treatments targeting candidate genes, time series experiments, and/or the development of specific assays intended to test hypotheses generated from gene expression experiments. These validation methods do not easily lend themselves to high-throughput processes and can often take as long as eighteen months to complete. Developing methods that allow for the objective, data driven identification of the key drivers of common human diseases would significantly enhance the utility of cellular constituent abundance measurement experiments in the target discovery process. More generally, such methods would also provide a framework for elucidating genetic networks.

Cellular constituent abundance data has recently been combined with other experimental data to allow for the more immediate identification of key drivers for complex disease traits. See, for example, Schadt et al., 2003, Nature 422, 297; Brem et al., 2002, Science 296, 752; and Klose et al., 2002, Nat. Genet. 30, 385, each of which is hereby incorporated by reference herein in its entirety. One such technique involves treating cellular constituent abundance data (e.g., gene expression data) as a quantitative trait in segregating populations. In such a method, chromosomal regions controlling the level of expression of a particular gene are mapped as abundance quantitative trait loci (eQTL). Abundance QTL that contain the gene encoding the mRNA (cis-acting eQTL) are distinguished from the other (trans-acting) eQTL, and those cis-acting eQTL that co-localize with chromosomal regions controlling a disease (clinical) trait (cQTL) are identified. The identification of a common chromosomal location for both cis-acting eQTL and a cQTL is used to nominate susceptibility loci for the disease trait. See, for example, Karp et al., 2000, Nat. Immunol 1, 221; Schadt et al. Nature 422, 297; and Eaves et al., 2002, Genome Res. 12, 232, each of which is hereby incorporated by reference herein in its entirety.

Overall, the development and widespread use of microarray technology in various scientific and medical disciplines has generated large amounts of abundance data for cellular constituents from numerous organisms. Also, the genome sequences of humans and several model organisms have established a nearly complete list of the genes required to enact cellular, developmental, and behavioral processes in these organisms (Goffeau et al., 1996, Science 274, 546; Myers et al., 2000, Science 287, 2196; Lander et al., 2001, Nature 409, 860; and Venter et al., 2001, Science 291, 1304, each of which is hereby incorporated herein by reference in its entirety). The next major challenges in genomic research is to elucidate the functions of the large fraction of cellular constituents whose functions are currently unknown and to discover how these cellular constituents interact to perform specific biological processes. DNA microarray experiments provide a first step towards the goal of uncovering the function of cellular constituents on a global scale. Cellular constituents are often co-regulated. For example, genes that encode proteins that participate in the same pathway or are part of the same protein complex often exhibit similar transcription or expression patterns. Clusters of cellular constituents with related functions also often exhibit expression patterns that are correlated under large numbers of diverse conditions in DNA microarray experiments (Eisen et al., 1998, Proc. Natl. Acad. Sci. U.S.A. 95, 14863; Hughes et al., 2000, Cell 102, 109; Kim et al., 2001, Science 293, 2087; and Segal et al., 2003, Nature Genet. 34, 166, each of which is hereby incorporated by reference herein in its entirety). Such co-regulations are often broadly regarded as interactions. Identifying the interactions between cellular constituents is critical to understanding the biology behind such data. See, for example, Stuart et al., 2003, Science 302, 249, which is hereby incorporated by reference herein in its entirety. These interactions, especially those that are highly conserved across experimental conditions and genetic backgrounds, provide critical information in revealing the most highly conserved and functionally important cellular constituents that may serve as drug targets.

Existing methods in the art for identifying the critical interactions between cellular constituents are often highly convoluted and inefficient. Such methods are also often impractical to apply to different systems. The results from the existing methods are often difficult to interpret. What is needed in the art are efficient and effective systems and methods for processing the available abundance data of cellular constituents.

3. SUMMARY OF THE INVENTION

The present invention addresses the shortcoming in the known art. Computer systems and methods for identifying important targets among a wealth of data from abundant numbers of cellular constituents are provided. Advantageously, the computer systems and methods of the present invention offer simple and efficient ways to identify cellular constituents that are involved in important biological processes such as, for example, inflammation and metabolism.

Systems and methods are provided for determining a functional relationship between two cellular constituents. In embodiments, in accordance with the present invention, a cellular constituent is a gene, a protein, an mRNA expressing a gene, or a cDNA of a gene. Specifically, the systems and methods comprise (a) generating a first cellular constituent correlation matrix of a first plurality of correlation coefficients according to a preselected order of cellular constituents; (b) applying the preselected order to generate a second cellular constituent correlation matrix of a second plurality of correlation coefficients; and (c) Optionally repeating the applying step one or more times, each time generating a different cellular constituent correlation matrix of a different plurality of correlation coefficients thereby forming a plurality of cellular constituent correlation matrices.

Generating a First Cellular Constituent Correlation Matrix of a First Plurality of Correlation Coefficients According to a Preselected Order of Cellular Constituents.

Each correlation coefficient in the first plurality of correlation coefficients represents a correlation between first cellular constituent abundance measurement data for a pair of cellular constituents from each of a plurality of organisms subject to a same experimental condition. Each correlation coefficient in the first plurality of correlation coefficients is computed for a different pair of cellular constituents. The first cellular constituent correlation matrix is generated according to a preselected order of the cellular constituents in the pairs of cellular constituents for which the first plurality of correlation coefficients has been computed. Each pair of cellular constituents comprises a first cellular constituent and a second cellular constituent.

Applying the Preselected Order to Generate a Second Cellular Constituent Correlation Matrix of a Second Plurality of Correlation Coefficients.

Each correlation coefficient in the second plurality of correlation coefficients represents a correlation between second cellular constituent abundance measurement data for pairs of cellular constituents for which the first plurality of correlation coefficients is computed. The second cellular constituent abundance measurement data are from each of a plurality of organisms subject to a second experimental condition. The second experimental condition differs from the first experimental condition.

Generating Different Cellular Constituent Correlation Matrices.

The applying step is optionally repeated one or more times. Each time a different cellular constituent correlation matrix of a different plurality of correlation coefficients is generated thereby forming a plurality of cellular constituent correlation matrices. Each different plurality of correlation coefficients is computed using cellular constituent abundance measurement data from a plurality of organisms where each plurality of organisms has been subject to different respective experimental conditions. When a conserved area among the plurality of cellular constituent correlation matrices is present, a functional relationship between the first cellular constituent and the second constituent is determined to be present. Alternatively, when a conserved area among the plurality of cellular constituent correlation matrices is not present, a functional relationship between the first cellular constituent and the second constituent is not determined to be present.

In some embodiments, the systems and methods of the present invention further comprises prior to step (a) a step of clustering the first plurality of correlation coefficients to determine the preselected order of cellular constituents.

In some embodiments, the first, second and different cellular constituent correlation matrices are two-dimensional, and the preselected order is the same along each axis of the first, second and different cellular constituent correlation matrices.

In some embodiments, the systems and methods of the present invention further comprises a step of computing the first, second and different pluralities of correlation coefficients.

In some embodiments, the systems and methods of the present invention further comprises assigning a visible color signal to each correlation coefficient, such that the nature of color reflects the value of the correlation coefficient.

In some embodiments, the systems and methods of the present invention further comprises displaying or outputting to a user, to a computer readable storage medium, or to a remote computer the cellular constituent correlations matrices, or an indication of whether a functional relationship is determined to be present between the first cellular constituent and the second cellular constituent.

In alternative embodiments, the systems and methods of the present invention also comprise (a) receiving a plurality of datasets; (b) computing a plurality of correlation coefficients for each respective dataset in the plurality of datasets; and (c) applying a preselected order of the plurality of cellular constituents to the plurality of correlation coefficients of each dataset in the plurality of datasets thereby forming a plurality of cellular constituent correlation matrices and identifying the presence of a conserved area among the matrices.

Receiving a Plurality of Datasets.

A plurality of datasets are received. Each respective dataset in the plurality of datasets comprises cellular constituent abundance measurement data for a plurality of cellular constituents from each of a plurality of organisms subject to an experimental condition. Different datasets are from organisms subject to different experimental conditions and comprise cellular constituent abundance measurement data for the plurality of cellular constituents.

In some embodiments, two or more datasets in the plurality of datasets further represent a different genetic cross between organisms. In some embodiments in accordance with the present invention, the predetermined experimental condition of each dataset in the plurality of datasets represents a different environmental background. In some embodiments in accordance with the present invention, the different environmental background of a dataset in the plurality of datasets is the result of an application of an experimental condition to each organism in the plurality of organisms in the dataset. In some embodiments in accordance with the present invention, the experimental condition is exposure of each organism in the plurality of organisms to a pharmacological agent. In some embodiments in accordance with the present invention, the experimental condition is exposure of each organism in the plurality of organisms to a drug candidate. In some embodiments in accordance with the present invention, the predetermined experimental condition of two or more datasets in the plurality of datasets represents the same environmental background.

In some embodiments in accordance with the present invention, the experimental condition is the introduction of an exogenous gene or splice variant of the gene into each organism in the plurality of organisms. In some embodiments in accordance with the present invention, the experimental condition is deletion of a gene from each organism in the plurality of organisms. In some embodiments in accordance with the present invention, the experimental condition is a change of a culture condition of each organism in the plurality of organisms. In some embodiments in accordance with the present invention, the experimental condition is a disease afflicting each organism in the plurality of organisms.

In some embodiments in accordance with the present invention, each organism in the plurality of organisms in a dataset in the plurality of datasets is a cell line, a cell culture, a tissue sample, an organ, or a multicellular organism. In some embodiments in accordance with the present invention, a cellular constituent in the plurality of cellular constituents of a dataset in the plurality of datasets is a gene, a protein, an mRNA expressing a gene, or a cDNA of a gene. In some embodiments in accordance with the present invention, each organism in the plurality of organisms in a dataset in the plurality of datasets is a mammal. In some embodiments in accordance with the present invention, the mammal is a *Homo sapien*.

Each respective dataset in the plurality of datasets is further represented by a plurality of correlation coefficients. Each correlation coefficient in the plurality of correlation coefficients for a respective dataset in the plurality of datasets represents a correlation between cellular constituent abundance measurement data for a pair of cellular constituents in the plurality of cellular constituents across the plurality of organisms of the respective dataset. In some embodiments in accordance with the present invention, each correlation coefficient in the plurality of correlation coefficients of a dataset in the plurality of datasets is a Pearson correlation coefficient.

In some embodiments in accordance with the present invention, a correlation coefficient in the plurality of correlation coefficients for a dataset in the plurality of datasets is a positive correlation. Alternatively, in some embodiments in accordance with the present invention, a correlation coefficient in the plurality of correlation coefficients for a dataset in the plurality of datasets is a negative correlation.

In some embodiments in accordance with the present invention, the plurality of organisms of a dataset in the plurality of datasets consists of 10 or more organisms. In some embodiments in accordance with the present invention, the plurality of organisms of a dataset in the plurality of datasets consists of 100 or more organisms. In some embodiments in accordance with the present invention, the plurality of organisms of a dataset in the plurality of datasets consists of 1000 or more organisms.

In some embodiments in accordance with the present invention, the plurality of cellular constituents of a dataset in the plurality of datasets consists of 10 or more cellular constituents. In some embodiments in accordance with the present invention, the plurality of cellular constituents of a dataset in the plurality of datasets consists of 100 or more cellular constituents. In some embodiments in accordance with the present invention, the plurality of cellular constituents of a dataset in the plurality of datasets consists of 1000 or more cellular constituents.

(b) Computing a Plurality of Correlation Coefficients for Each Respective Dataset in the Plurality of Datasets.

A plurality of correlation coefficients for each respective dataset in the plurality of datasets is computed. Each correlation coefficient in the plurality of correlation coefficients for a respective dataset in the plurality of datasets represents a correlation between cellular constituent abundance measurement data for a pair of cellular constituents in the plurality of cellular constituents across the plurality of organisms of the respective dataset. The pair of cellular constituents comprises a first cellular constituent and a second cellular constituent. Each correlation coefficient in the plurality of correlation coefficients is computed for a different pair of cellular constituents. In some embodiments in accordance with the present invention, each correlation coefficient in the plurality of correlation coefficients of a dataset in the plurality of datasets is a Pearson correlation coefficient.

In some embodiments in accordance with the present invention, a correlation coefficient in the plurality of correlation coefficients for a dataset in the plurality of datasets is a positive correlation. Alternatively, in some embodiments in accordance with the present invention, a correlation coefficient in the plurality of correlation coefficients for a dataset in the plurality of datasets is a negative correlation.

(c) Applying a Preselected Order of Cellular Constituents to Each Dataset in the Plurality of Datasets.

A preselected order of cellular constituents in the plurality of cellular constituents is applied to the plurality of correlation coefficients of each dataset in the plurality of datasets to form a plurality of cellular constituent correlation matrices. When a conserved area among the plurality of cellular constituent correlation matrices that comprises the first cellular constituent and the second cellular constituent is present, a functional relationship between the first cellular constituent and the second constituent is determined to be present. When a conserved area among the plurality of cellular constituent correlation matrices that comprises the first cellular constituent and the second cellular constituent is not present, a functional relationship between the first cellular constituent and the second constituent is not determined to be present.

Optionally Clustering the Correlation Coefficients.

In some embodiments, the plurality of correlation coefficients that represent a first dataset in the plurality of datasets are clustered to determine an order that is used as the preselected order of the plurality of cellular constituents in the first dataset. In some embodiments, a clustering map is generated and the order of cellular constituents corresponding to a clustering map is determined to be the preselected order of cellular constituents.

In some embodiments in accordance with the present invention, the clustering step clusters correlation coefficients in the plurality of correlation coefficients of the first dataset that represent a positive correlation. In some embodiments in accordance with the present invention, the clustering step clusters correlation coefficients in the plurality of correlation coefficients of the first dataset that represent a negative correlation.

In some embodiments in accordance with the present invention, the clustering step clusters correlation coefficients in the plurality of correlation coefficients of the first dataset by applying a two-dimensional agglomerative clustering procedure, applying a hierarchical clustering technique, applying a k-means technique, applying a fuzzy k-means technique, applying a Jarvis-Patrick clustering, applying a self-organizing map technique, principal component analysis (PCA), independent component analysis (ICA), canonical correlation analysis (CCA), or applying a neural network technique. In some embodiments in accordance with the present invention, the order is a two-dimensional ordering of the plurality of cellular constituents along two axes.

In some embodiments, the systems and methods of the present invention further comprises assigning a visible color signal to each correlation coefficient, such that the nature of color reflects the value of the correlation coefficient.

In some embodiments, the systems and methods of the present invention further comprises displaying or outputting to a user, to a computer readable storage medium, or to a remote computer the cellular constituent correlations matrices, or an indication of whether a functional relationship is determined to be present between the first cellular constituent and the second cellular constituent.

Computer Program Product.

In some embodiments, systems and methods in accordance with the present invention provide a computer program product for use in conjunction with a computer system. The computer program product comprises a computer readable storage medium and a computer program mechanism embedded therein. The computer program product also comprises the computer program mechanism for determining a relationship between two cellular constituents.

Specifically, the computer program mechanism comprises instructions for generating a first cellular constituent correlation matrix of a first plurality of correlation coefficients. Each correlation coefficient in the first plurality of correlation coefficients represents a correlation between first cellular constituent abundance measurement data for a pair of cellular constituents from each of a plurality of organisms subject to a same experimental condition. Each correlation coefficient in the first plurality of correlation coefficients is computed for a different pair of cellular constituents. The first cellular constituent correlation matrix is generated according to a preselected order of cellular constituents in the pairs of cellular constituents for which the first plurality of correlation coefficients is computed. Each pair of cellular constituents comprises a first cellular constituent and a second cellular constituent.

The computer program mechanism also comprises instructions for applying the preselected order to generate a second cellular constituent correlation matrix of a second plurality of correlation coefficients. Each correlation coefficient in the second plurality of correlation coefficients represents a correlation between cellular constituent abundance measurement data for the pairs of cellular constituents for which the first plurality of correlation coefficients is computed. The second cellular constituent abundance measurement data are computed from each of a plurality of organisms subject to a second experimental condition where the second experimental condition differs from the first experimental condition.

The computer program mechanism also comprises instructions for optionally repeating the applying step one or more times, each time generating a different cellular constituent correlation matrix of a different plurality of correlation coefficients and thereby forming a plurality of cellular constituent correlation matrices. Each different plurality of correlation coefficients is computed using cellular constituent abundance measurement data from a plurality of organisms where each plurality of organisms has been subject to different respective experimental conditions. When a conserved area among the plurality of cellular constituent correlation matrices is present, a functional relationship between the first cellular constituent and the second constituent is determined to be present. Alternatively, when a conserved area among the plurality of cellular constituent correlation matrices is not present, a functional relationship between the first cellular constituent and the second constituent is not determined to be present.

In some embodiments, the computer program mechanism also comprises instructions for assigning a visible color signal to each correlation coefficient, such that the nature of color reflects the value of the correlation coefficient.

In some embodiments, the computer program mechanism also comprises instructions for displaying or outputting to a user, to a computer readable storage medium, or to a remote computer the cellular constituent correlations matrices, or an indication of whether a functional relationship is determined to be present between the first cellular constituent and the second cellular constituent.

In alternative embodiments, systems and methods in accordance with the present invention provide a computer program product for use in conjunction with a computer system. The computer program product comprises a computer readable storage medium and a computer program mechanism embedded therein. The computer program product also comprises the computer program mechanism for determining a relationship between two cellular constituents. Specifically, the computer program mechanism comprises instructions for receiving a plurality of datasets. Each respective dataset in the plurality of datasets comprises cellular constituent abundance measurement data for a plurality of cellular constituents from each of a plurality of organisms subject to an experimental condition. Different datasets are from organisms subject to different experimental conditions and comprise cellular constituent abundance measurement data for the plurality of cellular constituents.

The computer program mechanism also comprises instructions for computing a plurality of correlation coefficients for each respective dataset in the plurality of datasets. Each correlation coefficient in the plurality of correlation coefficients for a respective dataset in the plurality of datasets represents a correlation between cellular constituent abundance measurement data for a pair of cellular constituents in the plurality of cellular constituents across the plurality of organisms of the respective dataset. The pair of cellular constituents comprises a first cellular constituent and a second cellular constituent. Each correlation coefficient in the plurality of correlation coefficients is computed for a different pair of cellular constituents.

The computer program mechanism also comprises instructions for applying a preselected order of cellular constituents to each dataset in the plurality of datasets. A preselected order of cellular constituents in the plurality of cellular constituents is applied to the plurality of correlation coefficients of each dataset in the plurality of datasets to form a plurality of cellular constituent correlation matrices. When a conserved area among the plurality of cellular constituent correlation matrices that comprises the first cellular constituent and the second cellular constituent is present, a functional relationship between the first cellular constituent and the second constituent is determined to be present. When a conserved area among the plurality of cellular constituent correlation matrices that comprises the first cellular constituent and the second cellular constituent is not present, a functional relationship between the first cellular constituent and the second constituent is not determined to be present.

The computer program mechanism also comprises instructions for optionally clustering the correlation coefficients.

In some embodiments, the computer program mechanism also comprises instructions for assigning a visible color signal to each correlation coefficient, such that the nature of color reflects the value of the correlation coefficient.

In some embodiments, the computer program mechanism also comprises instructions for displaying or outputting to a user, to a computer readable storage medium, or to a remote computer the cellular constituent correlations matrices, or an indication of whether a functional relationship is determined to be present between the first cellular constituent and the second cellular constituent.

Computer System.

In some embodiments, systems and methods in accordance with the present invention provide a computer system for determining a relationship between two cellular constituents. The computer system comprises a central processing unit; a memory, coupled to the central processing unit, that store instructions for determining a relationship between two cellular constituents. Specifically, the memory of the computer system stores instructions for generating a first cellular constituent correlation matrix of a first plurality of correlation coefficients. Each correlation coefficient in the first plurality of correlation coefficients represents a correlation between first cellular constituent abundance measurement data for a pair of cellular constituents from each of a plurality of organisms subject to a same experimental condition. Each correlation coefficient in the first plurality of correlation coefficients is computed for a different pair of cellular constituents. The first cellular constituent correlation matrix is generated according to a preselected order of cellular constituents in the pairs of cellular constituents for which the first plurality of correlation coefficients is computed. Each pair of cellular constituents comprises a first cellular constituent and a second cellular constituent.

The memory of the computer system also stores instructions for applying the preselected order to generate a second cellular constituent correlation matrix of a second plurality of correlation coefficients. Each correlation coefficient in the second plurality of correlation coefficients represents a correlation between second cellular constituent abundance measurement data for the pairs of cellular constituents for which the first plurality of correlation coefficients is computed. The second cellular constituent abundance measurement data are from each of a plurality of organisms subject to a second experimental condition where the second experimental condition differs from the first experimental condition.

The memory of the computer system also stores instructions for optionally repeating the applying step one or more times, each time generating a different cellular constituent correlation matrix of a different plurality of correlation coefficients and thereby forming a plurality of cellular constituent correlation matrices. Each different plurality of correlation coefficients is computed using cellular constituent abundance measurement data from a plurality of organisms where each plurality of organisms has been subject to different respective experimental conditions. When a conserved area among the plurality of cellular constituent correlation matrices is present, a functional relationship between the first cellular constituent and the second constituent is determined to be present. Alternatively, when a conserved area among the plurality of cellular constituent correlation matrices is not present, a functional relationship between the first cellular constituent and the second constituent is not determined to be present.

In some embodiments, the memory of the computer system also stores instructions for assigning a visible color signal to each correlation coefficient, such that the nature of color reflects the value of the correlation coefficient.

In some embodiments, the memory of the computer system also stores instructions for displaying or outputting to a user, to a computer readable storage medium, or to a remote computer the cellular constituent correlations matrices, or an indication of whether a functional relationship is determined to be present between the first cellular constituent and the second cellular constituent.

In alternative embodiments, systems and methods in accordance with the present invention provide a computer system for determining a relationship between two cellular constituents. The computer system comprises a central processing unit; a memory, coupled to the central processing unit, that store instructions for determining a relationship between two cellular constituents. Specifically, the memory of the computer system stores instructions for receiving a plurality of datasets. Each respective dataset in the plurality of datasets comprises cellular constituent abundance measurement data for a plurality of cellular constituents from each of a plurality of organisms subject to an experimental condition. Different datasets are from organisms subject to different experimental conditions and comprise cellular constituent abundance measurement data for the plurality of cellular constituents.

The memory of the computer system also stores instructions for computing a plurality of correlation coefficients for each respective dataset in the plurality of datasets. Each correlation coefficient in the plurality of correlation coefficients for a respective dataset in the plurality of datasets represents a correlation between cellular constituent abundance measurement data for a pair of cellular constituents in the plurality of cellular constituents across the plurality of organisms of the respective dataset. The pair of cellular constituents comprises a first cellular constituent and a second cellular constituent. Each correlation coefficient in the plurality of correlation coefficients is computed for a different pair of cellular constituents.

The memory of the computer system also stores instructions for applying a preselected order of cellular constituents to each dataset in the plurality of datasets. A preselected order of cellular constituents in the plurality of cellular constituents is applied to the plurality of correlation coefficients of each dataset in the plurality of datasets to form a plurality of cellular constituent correlation matrices. When a conserved area among the plurality of cellular constituent correlation matrices that comprises the first cellular constituent and the second cellular constituent is present, a functional relationship between the first cellular constituent and the second constituent is determined to be present. When a conserved area among the plurality of cellular constituent correlation matrices that comprises the first cellular constituent and the second cellular constituent is not present, a functional relationship between the first cellular constituent and the second constituent is not determined to be present.

The memory of the computer system also stores instructions for optionally clustering the correlation coefficients.

In some embodiments, memory of the computer system further stores instructions for assigning a visible color signal to each correlation coefficient, such that the nature of color reflects the value of the correlation coefficient.

In some embodiments, memory of the computer system further stores instructions for displaying or outputting to a user, to a computer readable storage medium, or to a remote computer the cellular constituent correlations matrices, or an indication of whether a functional relationship is determined to be present between the first cellular constituent and the second cellular constituent.

4. BRIEF DESCRIPTION OF THE DRAWINGS

Like reference numerals refer to corresponding parts throughout the several views of the drawings.

5. DETAILED DESCRIPTION

Widespread improvements in the microarray technologies have helped to generate large quantities of abundance data of cellular constituents. The systems and methods disclosed in the present application aim to identify key gene-gene interactions that form the basic scaffold of the genetic network in a cell by looking for the most conserved interactions between pairs of cellular constituents over multiple sets of large-scale experimental conditions.

5.1. Overview of the Invention

A significant aspect of drug discovery is the identification of cellular constituents that will serve as suitable drug targets in order to cure or alleviate specific diseases. The present invention provides computer systems and methods that are capable of parsing large amounts of cellular constituent abundance data in order to determine highly conserved interactions between cellular constituents. Such information can be used to identify cellular constituents as possible drug targets. For example, the invention provides a method of determining whether there is a functional relationship between a pair of (a first and a second) cellular constituents. A functional relationship is a similarity or identity of biological function between the two cellular constituents, for example, an indication that both cellular constituents function in the same cellular signaling pathway. Additional examples of a similar or identical biological function include but are not limited to metabolic functions such as cholesterol metabolism, cell cycle control, and participation in cell development and differentiation. Thus, when the biological function of one of the pair of cellular constituents is known and the biological function of the other cellular constituent is unknown, the method of the invention can be used to predict the biological function that is unknown to be the same as or related to that for the known if the method determines that a functional relationship between the two cellular constituents is present.

In a specific embodiment, the methods, computer program products, and computer systems of the invention comprise a step of communicating, displaying, or outputting, e.g., to a user (a human individual), a monitor, a computer readable storage medium, or to a remote computer, the result(s) of the methods of the invention, e.g., the formed cellular constituent correlation matrices and/or an indication of whether a functional relationship between cellular constituents is determined to be present.

The invention provides computer program products and computer systems that comprise instructions for performing any of the methods of the invention.

5.1.1. System Architecture

Figure 1:
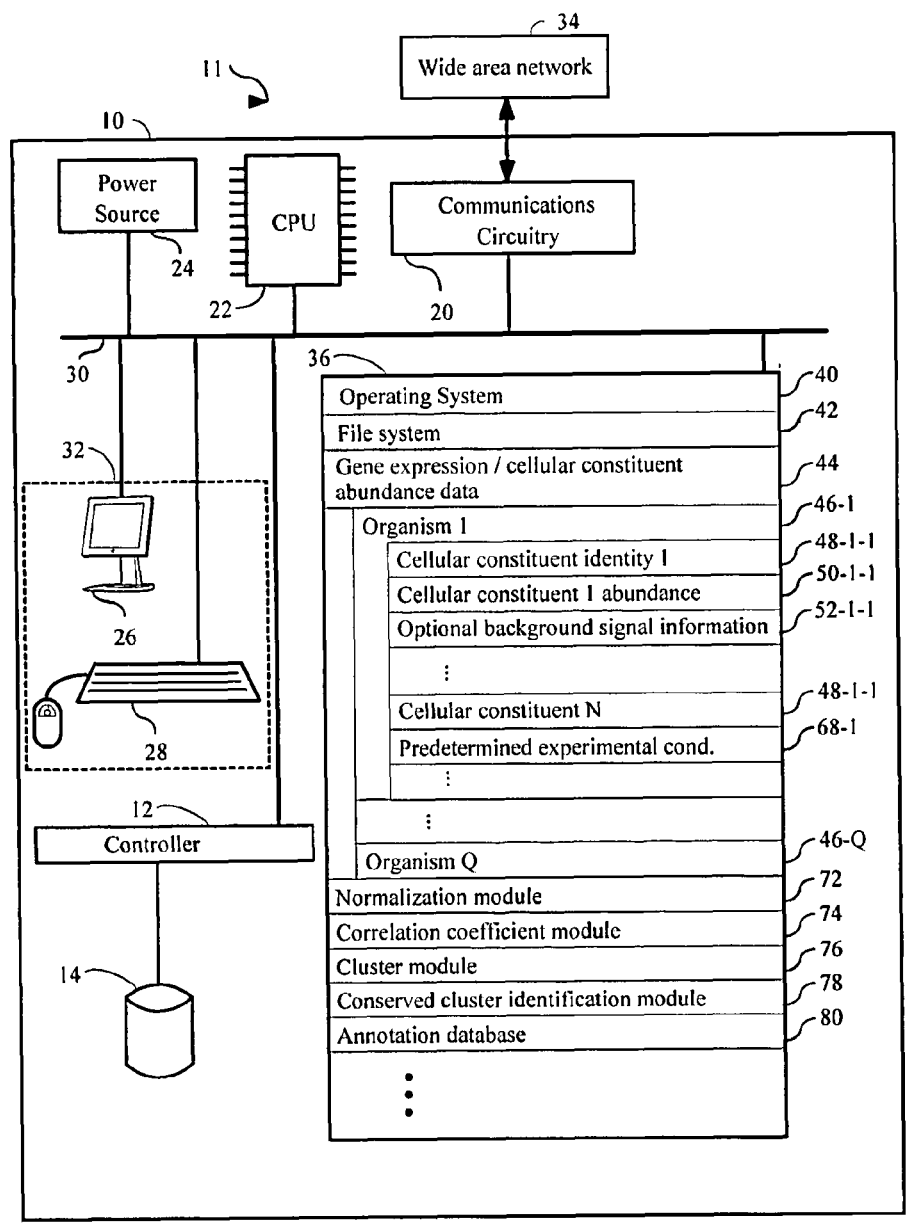
FIG. 1 illustrates a computer system in accordance with the present invention.

FIG. 1 illustrates an exemplary system 11 in accordance with an embodiment of the present invention. System 10 comprises at least one computer 10 (FIG. 1). Computer 10 comprises standard components including a central processing unit 22, memory (including high speed random access memory 36 as well as non-volatile storage, such as disk storage 14 that is controlled by controller 12) for storing program modules and data structures, user input/output device 32 (including display 26, mouse, and keyboard 28), a network interface 20 for coupling computer 10 to other computers via a communication network 34, one or more busses 30 that interconnect these components, and a power supply 24.

Memory 36 comprises a number of modules and data structures that are used in accordance with the present invention. It will be appreciated that, at any one time during operation of the system, a portion of the modules and/or data structures stored in memory 36 is stored in random access memory while another portion of the modules and/or data structures is stored in non-volatile storage 14. In a typical embodiment, memory 36 comprises operating system 40. Operating system 40 comprises procedures for handling various basic system services and for performing hardware dependent tasks. Memory 36 further comprises a file system 42 for file management. In some embodiments, file system 42 is a component of operating system 40.

5.1.2. Exemplary Method

Figure 2A:
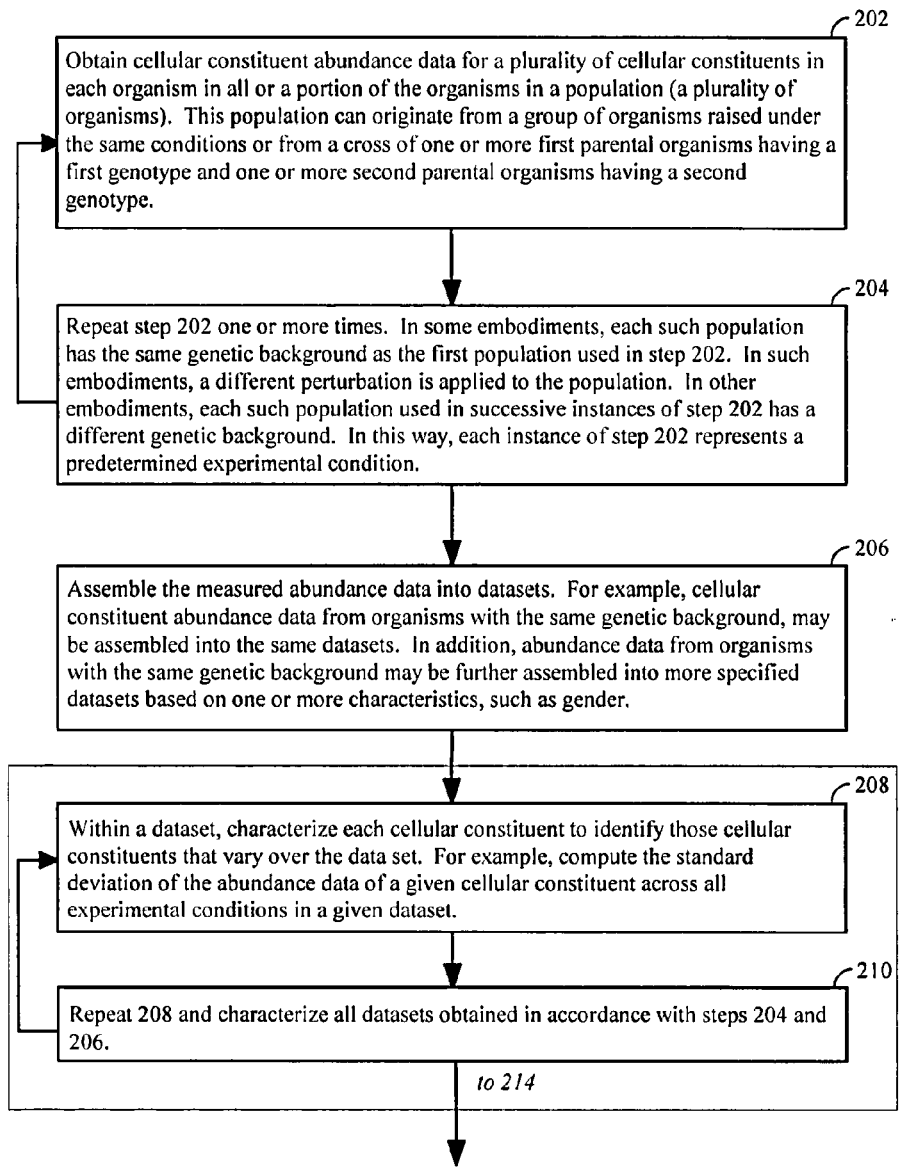
FIGS. 2A-2C illustrate an exemplary process for identifying conserved cellular constituents clusters among multiple cellular constituent abundance datasets, in accordance with an embodiment of the present invention.
Figure 2B:
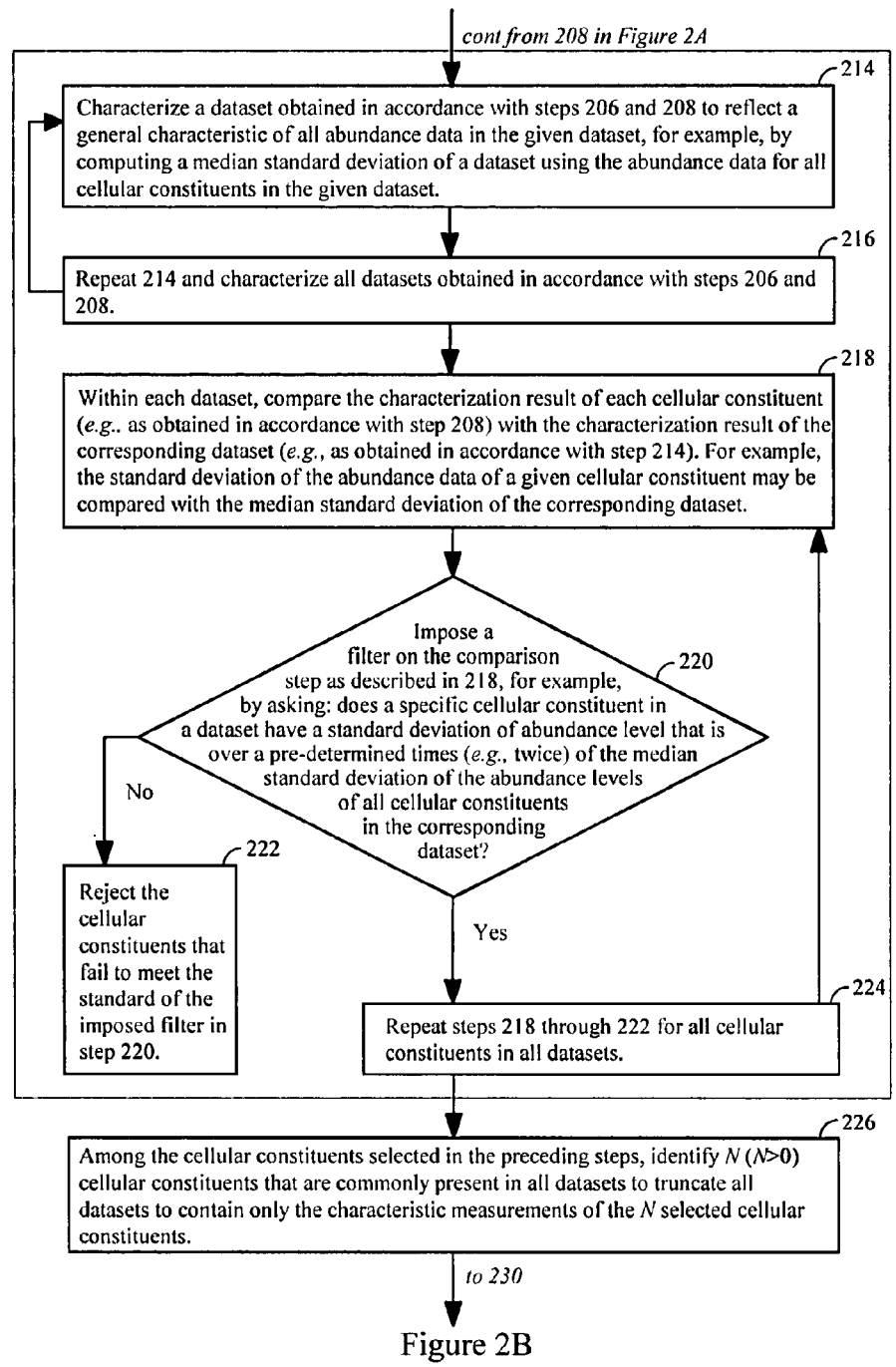
Figure 2C:
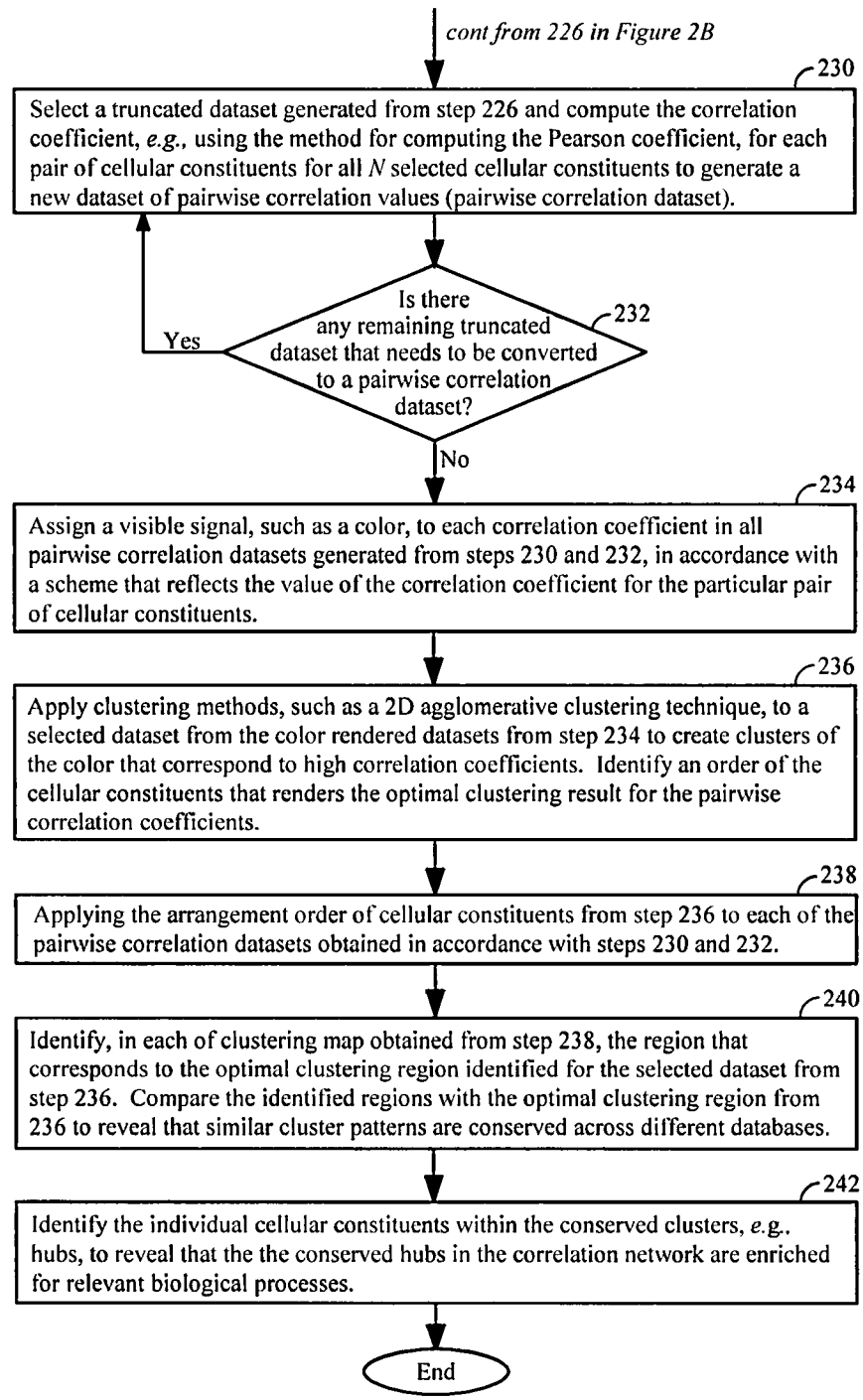

Now that an overview of a system in accordance with the present invention has been described, exemplary methods in accordance with the present invention will be described in conjunction with FIGS. 2A through 2C. The goal of the methods described in this section and summarized in FIGS. 2A through 2C is the identification of conserved clusters of cellular constituents (e.g., genes) whose expression levels are highly correlated with the expression levels of other cellular constituents. The conserved clusters of such cellular constituents are identified over multiple numbers of independent cellular constituent abundance datasets (e.g., 2 or more datasets, 10 or more datasets, 100 or more datasets, 1000 or more dataset, etc.). The significance of the conserved clusters correlates with the number of datasets examined. For example, the interaction between a pair of cellular constituents may be more important than the interaction between another pair of cellular constituents if the first interaction is conserved among 20 different datasets while the second interaction is conserved among 15 different datasets.

Referring to FIG. 2, steps 202 through 208 summarize exemplary processes for creating datasets that contain the abundance data of target cellular constituents. In some instances, such data is obtained from microarrays of target organisms. Section 5.7 describes suitable methods for obtaining cellular constituent abundance datasets for use in the systems and methods of the present invention.

Step 202.

In step 202 abundance data for a plurality of cellular constituents in each organism in all or a portion of the organisms in a population is received or otherwise obtained. In some embodiments, such data is stored in computer 10 (FIG. 1) as gene expression/cellular constituent data 44. For example, in one embodiment, for each organism 46 from which data is obtained, cellular constituent identity 48, cellular constituent abundance 50, and optional background signal information 52 is received and stored in the memory of computer 10. In some embodiments in which the measurement data is microarray data, the data may be normalized using normalization module 72. Exemplary normalization methods are disclosed in Section 5.3. For example, the data may be processed and normalized using techniques disclosed in Section 5.3 and/or Draghici, 2003, *Data Analysis Tools for DNA Microarrays*, Chapman & Hall, New York, which is hereby incorporated by reference herein in its entirety. As used herein, the step of receiving includes, but is not limited to, making measurements and/or obtaining data from either a local or remote memory source (e.g., over the Internet). In some embodiments in accordance with the present invention, cellular constituent abundance data is measured for all or a substantial portion (e.g., more than 60 percent of the genes in the genome of the species under observation) of the cellular constituents that are present in each respective organism in a group of organisms in a single species that are raised under the same conditions. Exemplary species include, but are not limited to, yeasts, *C. elegans*, mouse, dog, cats, pigs, non-human mammals, humans, etc. In some embodiments, cellular constituent abundance data is received from one or more tissues and/or organs in each such organism. Exemplary tissues and/or organs include, but are not limited to, liver, brain, stomach, kidney, heart, and adipose tissue. Alternatively, cellular constituent abundance data is measured from progeny (e.g., F$_2$, etc.) of a cross of one or more parental organisms having different genotypes. In some embodiments in accordance with the present invention, cellular constituent abundance data is measured for all or a substantial portion (e.g., at least 50 percent, at least 60 percent, at least 70 percent, at least 80 percent, at least 90 percent) of the cellular constituents that are present in progeny of a particular genetic cross.

In some embodiments, cellular constituent abundance data is obtained for one or more tissue types of an organism of the same genetic background, for example, the liver tissue of a group of mice that have undergone the same genetic crosses. Cellular constituent abundance data can also be measured for a group of organisms of the same genetic background but that are raised under different experimental conditions. In some embodiments, the cellular constituent abundance data is measured. In some embodiments, such data is already available and is simply obtained using, for example, electronic means from a database of such data.

Step 204.

Step 202 is repeated a number of times. Each time step 202 is repeated, abundance data for cellular constituents from a population of organisms of the same genetic background as the original population of organisms, but raised under different experimental conditions, is obtained. In this way, a plurality of datasets is constructed, where each data structure represents a predetermined experimental condition and comprises cellular constituent abundance measurement data for a plurality of cellular constituents from each of a plurality of organisms. The predetermined experimental condition associated with each data set is stored as the corresponding predetermined experimental condition 68 in the memory of computer 10. Exemplary experimental conditions include, but are not limited to, differences in dietary conditions, temperature, exposure to chemical compounds, exposure to gene specific siRNA, vaccinations, exposure to antibodies, etc. Specific exemplary experimental conditions include, but are not limited to, environmental (e.g., high-fat diet versus low-fat diet), variation in drug testing conditions (e.g., exposure to test compounds versus exposure to placebos), and variations in genetic background (e.g a specific gene knock-out versus absence of a specific gene knock-out, over-expressing or under-expressing a specific genes or a group of specific genes). Still, alternatively, in the case where the organism is a cellular organism such as yeast, cellular constituent abundance data can be obtained from first organisms that are grown at a first temperature (e.g., 30° C.) versus second organisms that are grown at a second temperature (e.g., 25° C.) where each such temperature represents a predetermined experimental condition. In some embodiments, experimental conditions further comprise one or more biological states (e.g., a group of patients with stage 1 lung cancer), one or more organs, or one or more tissues or tissue types (e.g., blood, adipose, or muscle). Cells within one or more tissues may be contiguous at cell walls (e.g., plants) or membranes (e.g., blood). Cells within one or more tissues may be of all of one type as a simple tissue (e.g., squamous epithelium, plant parenchyma) or of more than one type as a mixed tissue (e.g., connective tissues, xylem, phloem, etc.).

In some embodiments, populations for use in the multiple instances of step 202 are each obtained by applying various experimental conditions to organisms that are all obtained from the same genetic cross. In this way, although each population applied to a successive instance of step 202 has the same genetic background, each such population is subjected to a different experimental condition, thereby achieving the goal of having each dataset collected in an instance of step 202 representing a predetermined experimental condition.

The predetermined experimental condition for each dataset can be the same or different as the predetermined experimental condition for other datasets. In some embodiments, accordingly, multiple gene expression datasets are received from a population of organisms from a cross of one or more first parental organisms having a different first genotype and one or more second parental organisms having a different second genotype.

In some embodiments in accordance with the present invention, cellular constituent abundance data is obtained from any combination of numerous existing databases around the world. For example, cellular constituent abundance data is available at public accessible databases such as Gene Expression Omnibus at the National Institute of Health) and ArrayExpress at the European Bioinformatics Institute.

DNA microarray data can also be obtained from databases such as the Stanford Microarray Database, the Functional Genomics Core Laboratories at the University of California at San Francisco, and the Yale Microarray database at Yale University.

Step 206.

Upon completion of steps 202 and 204, raw abundance data is sorted and assembled into datasets. In some embodiments, cellular constituent abundance data from organisms with the same genetic background, regardless of the experimental conditions applied, is assembled into the same dataset. Cellular constituent abundance data from organisms with the same genetic background can further be assembled into more specific datasets based on characteristics such as gender. In preferred embodiments, abundance data from organisms having the same genetic background and the same experimental conditions are localized to the same dataset rather than dispersing such data across multiple datasets. In this way, the datasets constructed in step 206 are mutually exclusive. For example, abundance data for liver samples of wild type males fed on a high-fat diet will only be placed in a single dataset. After step 206, cellular constituent abundance data from a plurality of target cellular constituents under multiple experimental conditions are assembled into mutually exclusive datasets.

In some embodiments, each dataset comprises cellular constituent abundance data for 10 or more cellular constituents, 100 or more cellular constituents, 1000 or more cellular constituents, 2000 or more cellular constituents, more than 5000 cellular constituents, more than 10000 cellular constituents, between 10 and 25,000 cellular constituents, or less than 10,000 cellular constituents. In some embodiments, each dataset represents cellular constituent data for between 2 and 20 organisms, more than 5 organisms, more than 10 organisms, more than 20 organisms, more than 100 organisms, between 5 and 1000 organisms, or less then 50 organisms. In some embodiments, a dataset comprises data from one or more of the populations constructed in step 204, between two and five of the populations constructed in step 204, or less than ten of the populations constructed in step 204.

Step 208.

In step 208, the abundance data are analyzed to determine which cellular constituents vary significantly across datasets. In some embodiments in accordance with the present invention, such variation is identified for a respective cellular constituent by computing the standard deviation of the abundance data of the respective cellular constituent across a given dataset. For example, consider the case in which liver expression data for/cellular constituents from mice liver is measured across m different experimental conditions. For a given cellular constituent (e.g., $G_i$, where $1 \leq i \leq l$, the value of with respect to the size of the dataset; both l and i are integers), a standard deviation $\sigma_{Gi}$ is computed using the cellular constituent abundance data of $G_i$ from all m experimental conditions.

The cellular constituent abundance data for the same cellular constituent in different datasets is expected to have different standard deviation values due to changes in experimental conditions. Hence, differences in standard deviation values for the same cellular constituent across different datasets also quantify the effects of experimental variations.

Step 210.

In step 210, the characterization process of step 208 is repeated for each cellular constituent in every dataset under consideration.

Step 214.

In step 214, the characterization of the cellular abundance levels is also performed at the dataset level. In some embodiments in accordance with the present invention, a median standard deviation value $\overline{\sigma}_{Dj}$ is computed for each dataset to reflect the average quality of the entire given dataset $D_j$ ($1 \leq j \leq p$, where p represents the number of datasets assembled after step 208; and both p and j are integers).

Step 216.

In step 216, the characterization process of step 214 is repeated for each cellular constituent in every dataset under consideration.

Optional Step 218.

In optional step 218, the standard deviation of the abundance data of a given cellular constituent $\sigma_{Gi}$ (e.g., as obtained in steps 208 and 210) is compared with the median standard deviation of the corresponding cellular constituent abundance dataset $\overline{\sigma}_{Dj}$ (e.g., as obtained in steps 214 and 216). As will be seen below, this allows for the removal from consideration of any cellular constituents that did not vary significantly across the dataset. In steps 218 through 224, the results from two different characterization analyses is compared to select only the abundance data that satisfy one or more imposed filters. Within each dataset, the characterization result of each cellular constituent (e.g., as obtained in accordance with step 210) will be compared with the characterization result of the corresponding dataset (e.g., as obtained in accordance with step 214).

Step 220.

In step 220, a filter is applied to assess the quality of every cellular constituent in a given dataset. For example, in a given dataset (e.g., $D_j$ where $1 \leq j \leq p$), when the standard deviation of the cellular constituent abundance of a particular cellular constituent $G_i$ (e.g., $\sigma_{Gi}$) is compared with the median standard deviation value $\overline{\sigma}_{Dj}$ of that dataset, has to be over a pre-determined times of $\overline{\sigma}_{Dj}$ in order to remain in the dataset for subsequent analysis. In some embodiments in accordance with the present invention, the pre-determined times is two times (e.g., as described in step 220). More specifically, the standard deviation of the abundance data of a given cellular constituent ($\sigma_{Gi}$) needs to be equal or greater than a predetermined number of times (e.g., two, three, four, or five times) of the median standard deviation ($\overline{\sigma}_{Dj}$) to remain in the dataset for subsequent analyses. In other embodiments in accordance with the present invention, $\sigma_{Gi}$ only needs to exceed 1.5, 1.6, 1.7, 1.8, 1.9, 2.0 or more times of $\overline{\sigma}_{Dj}$ to remain in subsequent analyses. In other embodiments in accordance with the present invention, $\sigma_{Gi}$ may need to be over three times, over four times, or over five times of $\overline{\sigma}_{Dj}$ to remain in subsequent analyses.

Step 222.

In step 222, the cellular constituents that fail to meet the standard of the set filter (220—No) will be rejected from future analysis. Step 222 is applied as a quality control step to reject cellular constituent abundance data from the cellular constituents under consideration when they do not vary significantly under the experimental conditions.

Step 224.

The filtering process is repeated for every cellular constituent in every dataset (e.g., step 224). After a filter is applied to all datasets, each dataset will potentially contain a smaller number of cellular constituents than the number of cellular constituents that are originally assembled into the given dataset. Step 224 is applied to ensure every dataset is held to the same quality standard. It is possible that by varying the predetermined value at step 220, the sizes of the different datasets of cellular constituents may also be varied to include more or less cellular constituent abundance data.

Step 226.

In step 226, the cellular constituents that have satisfied the imposed filter are identified for each dataset. Among these selected cellular constituents, a common set of N cellular constituents will be further identified to truncate all datasets to contain only the abundance data of these N common cellular constituents. By doing so, all datasets are truncated to the same size such that all of them now only contain the abundance value measured for the N common cellular constituents. The number N can be any number. For example, the number N, can be 10 or more, 20 or more, 30 or more, 40 or more, 50 or more, between 10 and 50, 60 or more, 100 or more, 200 or more, 500 or more, between 10 and 500, 1000 or more, or less than 25,000.

To provide an exemplary illustration, consider the case where there are a total of three datasets. A filter of two times the median standard deviations (e.g., cellular constituents in each dataset have to have standard deviations greater than two times of the median standard deviation of each datasets, $\bar{\sigma}_D 1$, $\bar{\sigma}_D 2$, and $\bar{\sigma}_D 3$, to remain in subsequent analysis) is applied to each respective dataset. After the filter, dataset one contains a selected group of 150 cellular constituents that have satisfied the filter; dataset two contains a selected group of 250 cellular constituents that satisfy the filter; and dataset three contains a selected group of 350 cellular constituents that satisfy the filter. There are, however, only 100 cellular constituents that are found in all three selected groups of cellular constituents. In each of the three datasets, the expression data of those cellular constituents other than the 100 common cellular constituents are further rejected from the subsequent analyses. Hence, all three datasets are now truncated to the same size: e.g., each of them only contains the expression level data for those 100 selected cellular constituents. Restricting attention to this common cellular constituent set is important for the subsequent steps to facilitate a more natural comparison of the topological properties of the co-expression networks over the different datasets.

Although these characterization steps (e.g., steps 208 through 216) are informative in assessing the quality of the datasets, they are optional and, in some embodiments, are not performed. Likewise, filtering steps (e.g., 218 through 224) are optional and are not performed in some embodiments. These characterization and filtering steps are effective in parsing large amounts of abundance data to quickly select the information that is most relevant for subsequent analyses. They are therefore of great importance in enhancing the performance of the computational systems and methods in accordance with the present invention. As computing power improves, such parsing steps may not be needed for a satisfactory computational speed. Furthermore, the characterization and the filtering steps are implemented in some embodiments in accordance with the present invention based on certain hypotheses. For example, the filter is imposed to identify only those cellular constituents that vary significantly across the experimental conditions. It is hypothesized that only the highly variable cellular constituents have greater potential to produce statistically significant cellular constituent pair correlations. Such hypotheses are subject to change depending on available biological data and the understanding of the biological systems of interest. In addition, the methods of identifying such significant cellular constituents are also subject to change with the improvement of mathematical tools. Finally, it is also possible that important information is omitted when such characterization and filtering steps are applied to the datasets. In some embodiments in accordance with the present invention, the choices will be given, for example, as menu options of software programs in accordance with the systems and methods of the present invention, to users of the software. The users will then determine whether such restriction steps will be included in their analyses.

Figure 2D:
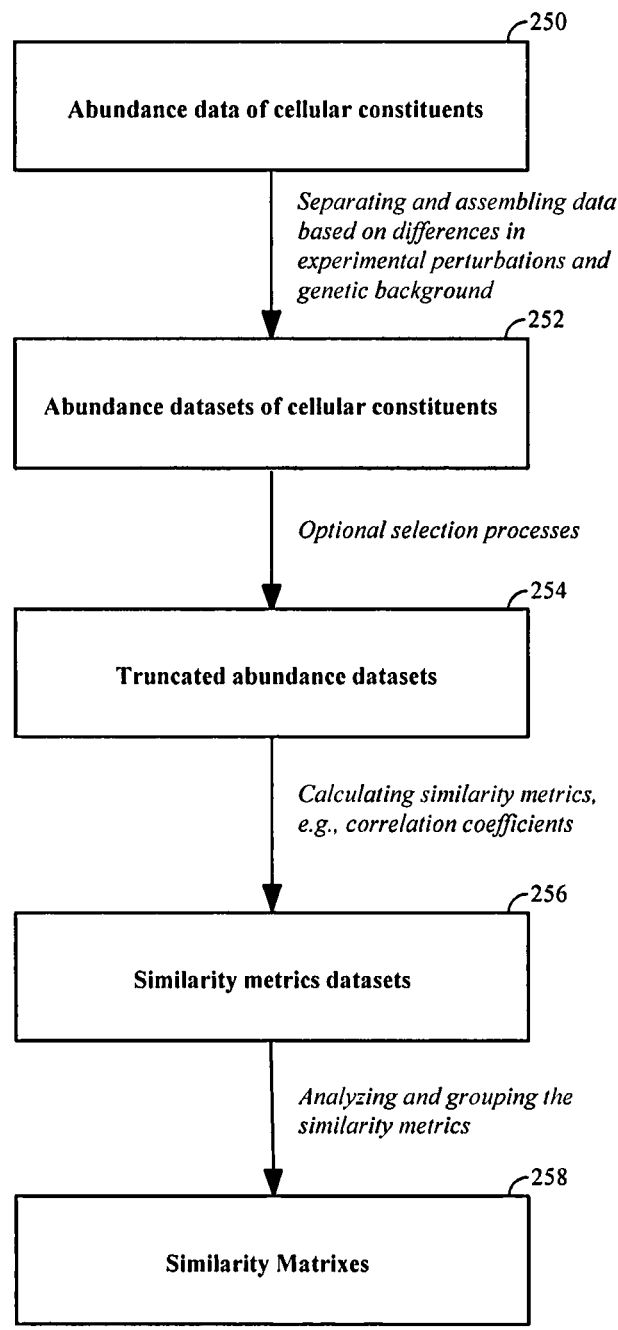
FIG. 2D illustrates data processing steps in accordance with an embodiment of the present invention.

After steps 226, the original datasets of cellular constituent abundance data are truncated to include only the cellular constituent abundance data above a predetermined quality level. Alternatively, a common set of cellular constituents can be selected by other methods or other types of filters. Also alternatively, a common set of cellular constituents can be selected by simple presence among all datasets without applying additional characterization methods or filters. For example, selected steps of characterization may be omitted (e.g., steps of 208 through 224 as shown in dashed rectangles in FIGS. 2A and 2B). These examples of optional selection processes as illustrated in FIG. 2D.

Step 230.

In step 230, correlation coefficients will be computed for every pair of cellular constituents for each truncated dataset containing the measurements of the abundance data for N cellular constituents. In some embodiments, correlation coefficient module 74 (FIG. 1) is used to perform such computations. The methods for computing pairwise correlation coefficients are discussed in detail in Section 5.2. Prior to step 230, the datasets contain one-dimensional cellular constituent abundance data that correspond to specific cellular constituents. After step 230, a dataset of cellular constituent abundance data is converted to a new dataset of pairwise correlation coefficients (e.g., pairwise correlation datasets). The new pairwise correlation datasets are two-dimensional similarity metrics datasets in that they describe properties of pairs of cellular constituents rather than individual cellular constituents.

Step 232.

In step 232, the correlation coefficient calculation as described in step 230 is repeated for each pair of cellular constituents in each truncated dataset. After the correlation coefficients are computed, the datasets that contain the measurements of abundance data of N cellular constituents are converted to new pairwise correlation datasets that contain W unique pairwise correlation coefficients (W=N*(N−1)/2). For example, a truncated dataset of 100 cellular constituents will render a new pairwise correlation dataset that contains 4950 pairwise correlation coefficients. A perfectly positively correlated cellular constituent pair has a Pearson correlation coefficient of 1, while the perfectly negatively correlated cellular constituent pair has a Pearson correlation coefficient of −1. A positive value thus suggests positive correlation and a negative value suggests negative correlation. Entirely non-related cellular constituent pairs usually have a Pearson correlation coefficient around 0.

Besides being the most straightforward method for evaluating the relations between two cellular constituents, uses of a Pearson correlation has other advantages. First, the diverse datasets of abundance data measurements for the cellular constituents are converted to values between −1 and 1, which simplifies subsequent analyses. Second, the process of calculating the correlation coefficient is similar to the process of calibration. However, the present invention by no means is limited to the use of Pearson correlations. Any pattern classification technique can be used to characterize the functional relationship between pairs of cellular constituents in accordance with the present invention.

In some embodiments in accordance with the present invention, Pearson correlation coefficients are computed using the mean log ratio of the abundance data of the cellular constituents. The mean log ratios (mlratio) of cellular constituent abundance data are introduced to eliminate color bias associated with the fluorescent dye signals of the cellular constituent chips during microarray analysis. For example, in a typical microarray experiment, the "experiment" is labeled with a red dye and the "control" is labeled with a green dye. What is normally measured on the microarray is the ratio of experiment and control measurements (e.g., experiment/control) or equivalently as log(experiment/control). However, it is known that the measured ratios might be dominated by dye color bias. To effectively reduce or eliminate this bias, a second chip with samples labeled with the opposite colors was added for each microarray experiment. The results of the second sets of measurements can be expressed as log(control/experiment). A mathematical average of the two sets of log ratios from the corresponding color swapped measurements can be expression as a mean log ratio (mlratio), where mlratio=0.5*{log(experiment/control)−log(control/experiment)}. The quantity of mlratio enters into all subsequent computations. In some embodiments in accordance with the present invention, Pearson correlation coefficients of cellular constituents may be computed in different ways, for example, as pairwise correlation coefficients between the abundance data of cellular constituents within the same dataset, or as a generalized correlation coefficient between the pairwise correlation coefficients from two different datasets. A pairwise correlation coefficient can be computed between cellular abundance data of any pair of cellular constituents within a dataset. For example, in some embodiments, the abundance data obtained under various experimental conditions are used in computing a pairwise correlation coefficient for any pair of cellular constituents. Alternatively, a generalized correlation coefficient can be computed between two datasets after pairwise correlation coefficients have been computed for pairs of cellular constituents within those datasets. For example, dataset D1 comprises abundance data of a plurality of cellular constituents. Dataset D2 also comprises abundance data of a plurality of cellular constituents, for example, obtained from animals of the same species with a different genetic background. The cellular constituents that are present in both the D1 and D2 datasets thus constitute a common set of cellular constituents. Within dataset D1, pairwise correlation coefficients can be computed for each pair of cellular constituents in the common set of cellular constituents, thus creating a first new dataset of correlation coefficients, for example, matrix C1. Similarly, within dataset D2, pairwise correlation coefficients can be calculated for each pair of cellular constituents with the common set of cellular constituents, thus creating a second new dataset of correlation coefficients, for example, matrix C2. Because correlation matrices C1 and C2 are based on a common set of cellular constituents, they have similar size and no longer contain explicit dependence on the individual experimental conditions associated with original datasets D1 and D2. Therefore, these two matrices may be used to compute a generalized correlation coefficient. For example, the pairwise correlation coefficient of cellular constituent A and B in matrix C1 is directly compared to that of the same two cellular constituents in matrix C2. The process is repeated for every pairwise correlation coefficient in matrix C1 against a corresponding pairwise correlation coefficient in matrix C2 to give rise to a generalized correlation coefficient between matrices C1 and C2. The generalized correlation coefficient reflects the correlation between correlation coefficients. It may be indicative of the similarity of intrinsic wiring of the two datasets D1 and D2.

Step 234.

At step 234, a signal (e.g., a visible signal such as a color) is assigned to each generated correlation coefficient, such that the nature of the signal reflects the value of the correlation coefficient. For example, in some embodiments in accordance with the present invention, a color scheme is provided where bright red represents perfectly positive correlation (e.g., a correlation coefficient of 1), bright blue reflects perfectly negative correlation (e.g., a correlation coefficient of −1), and black reflects correlation coefficients that are equal to 0. A warm color spectrum gradient is then assigned to the correlation coefficient values between 0 and 1 and a cold color spectrum gradient is correspondingly assigned to the correlation coefficient values between −1 and 0.

Step 236.

Once visible signals are assigned to the pairwise correlation coefficients, clustering methods (e.g., a two-dimensional agglomerative clustering technique) may be applied to cluster the colors representing high correlation coefficients in step 236. In some embodiments, such clustering is performed using cluster module 76 (FIG. 1). Detailed descriptions of available clustering techniques are included in Section 5.5, below. A brief example is given here to illustrate the clustering process of a pairwise correlation coefficient dataset from step 234 using a two-dimensional agglomerative clustering algorithm. One of the pairwise correlation coefficient datasets is selected as the model dataset. There are no special requirements for the model dataset. It is therefore possible to pick any of the M datasets that have been generated after the signal assignment (e.g., post step 234). After a dataset is selected, a two-dimensional grid map of $N^2$ grids (N×N) is drawn. In some embodiments, the two-dimensional grid map is formed by two orthogonal axes that each contains N units where N represents N cellular constituents that are selected from the characterization and filtering steps (e.g., steps 220 to 226). Names of the N cellular constituents, with no requirement that they bin in a particular order, are assigned to the N units on the first axis of the two-dimensional grids. Alternatively, values or symbols corresponding to the N cellular constituents, also with no requirement that they be in a particular order, can be assigned to the N units on the first axis of the two-dimensional grids. Subsequently, the names of the N cellular constituents, in the same order that has defined the assignment of the first axis, will be assigned to a second and orthogonal axis of the two-dimensional grids. As a result, a symmetrical grid map forms with each grid representing the intersection of a pair of cellular constituents. The assigned color corresponding to the correlation coefficient of a given pair of cellular constituents will be filled into the grid that corresponds to the given pair of cellular constituents. The agglomerative clustering method will then be applied to re-arrange the colored grids so that grids corresponding to high correlation coefficients are moved adjacent to each other. Because of the symmetrical nature of the grid maps, the units on the two orthogonal axes remain identical to each other regardless of the changes in the specific orders of the cellular constituents which are represented by the these units. When the optimal cluster pattern is achieved, as judged by the clustering methods, the order of the cellular constituents that renders such optimal results is identified and recorded (e.g., 236).

Figure 4A:
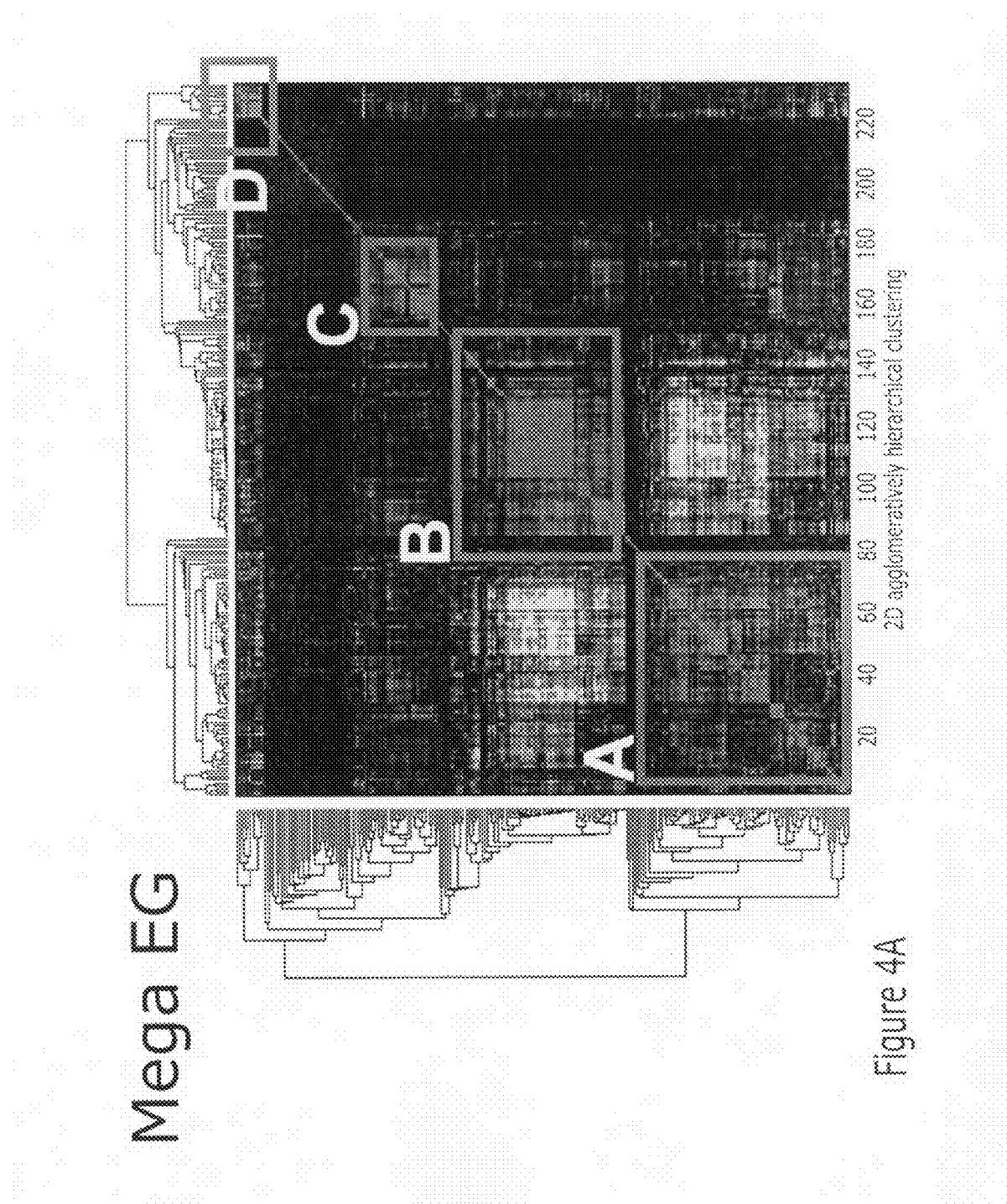
FIG. 4A illustrates a dataset after a two-dimensional agglomerative clustering procedure in accordance with an embodiment of the present invention.

By way of illustration, the clustering example presented in FIG. 4A from Section 6 groups the two-dimensional grid map by the correlation coefficients that correspond to strong positive correlations between cellular constituents. The scope of the present application, however, is not limited to the application. In some embodiments in accordance with the present invention, the correlation grid map can be grouped according to the strong negative correlations between cellular constituents.

Step 238.

In step 238, the arrangement order of cellular constituents obtained from step 236 are applied to the other pairwise correlation datasets that contain data related to the same N cellular constituents. In typical embodiments, the clustering step is omitted from the process. Instead, grid maps of the other datasets are drawn using the order of the cellular constituents that has rendered the optimal cluster pattern in step 236. Using the same order, grid maps are drawn for all pairwise correlation datasets. After step 238, the two-dimensional similarity metrics datasets from step 230 are further converted to maps of similarity matrices that can be visualized.

In some embodiments, clustering of the first pairwise correlation dataset is not required. Instead, a randomly selected order of cellular constituents is applied to all pairwise correlation datasets to generate, for example, a two-dimensional grid map. Additional computing methods may then be applied to identify any similarities among, for example, the resulting two-dimensional grid maps.

Step 240.

In step 240, multiple grid maps from different correlation datasets are compared to reveal any conserved clusters of correlation coefficients. In some embodiments, step 240 is performed in whole or part using conserved cluster identification module 78 (FIG. 1). The same regions are highlighted in other grid maps so that comparison may be directly made between the grid maps. Without intending to be limited to any particular theory, it is believed that the most crucial interactions between cellular constituents are conserved across populations of organisms under several different experimental conditions. Therefore, it is expected that similar clustering patterns should be identified for grid maps built from datasets other than the model dataset in step 240. In some embodiments in accordance with the present invention, all datasets are truncated to the same size, so it is simple to identify the most conserved interactions between pairs of cellular constituents as clusters along the diagonal axis of the two-dimensional grid map.

Step 242.

In step 242, the cellular constituents in the most conserved blocked in the grid maps are annotated and the most conserved cellular constituent-cellular constituent interactions are identified (e.g., as demonstrated in FIGS. 4A through 4E). In some embodiments, such annotation data is stored in annotation database 80 (FIG. 1). In some embodiments in accordance with the present invention, these highly conserved clusters are called cellular constituent hubs. The cellular constituents identified as part of the highly conserved cellular constituent-cellular constituent network are thus named hub cellular constituents. In some embodiments in accordance with the present invention, the conserved cellular constituent clusters are highly enriched with cellular constituents that are essential for important biological processes such as various metabolic processes including, but not limited to, the diseases and conditions described in Section 5.4, below.

Steps 250 to 258: Evolution of the Datasets. To clarify data flow in accordance with some embodiments of the present invention, FIG. 2D illustrates how raw abundance data for cellular constituents (e.g., 250) are transformed into correlation grid maps or similarity matrices (e.g., 258). Abundance data for cellular constituents, such as protein expression level, gene transcription level, and/or enzyme activities level, are separated and assembled into datasets (e.g., 252). There are numerous ways of assembling the datasets. In some embodiments, in accordance with the present invention, similar abundance data, e.g., that is generated from similar experimental conditions or from organisms of the same genetic background, will not be assembled into multiple datasets. This additional requirement ensures that the network of cellular constituents defined in subsequent steps truly reflect the nature of their interactions rather than the result of mere similar experimental results. Optional selection processes may then be applied to the assembled datasets to render truncated datasets (e.g., 254). While this procedure reduces the amount of data in the system and simplifies subsequence procedures, the truncation step is not required.

Datasets of abundance data, truncated or not, are transformed into similarity metrics datasets (e.g., 256). At this step, the one-dimensional abundance datasets are converted into two dimensional pairwise metrics datasets. The similarity metrics, in some embodiments in accordance with the present invention, are defined as correlation coefficients. One advantage in converting one dimensional abundance datasets into two dimensional metrics datasets is the two dimensional dataset provide clear visual representation of relations between the individual cellular constituents. In addition, through this conversion, the wide range of abundance data are converted to a new set of values that are within reasonable range and easy to manipulate. Following the construction of similarity metrics datasets, methods such as clustering techniques, are applied to analyze and group the similarity metrics.

5.2. Methods for Computing Similarity Metrics Data

Similarity metrics describe the relations between pairs of cellular constituents. The following subsections provided nonlimiting examples of similarity metrics that can be computed between pairs of cellular constituents.

5.2.1. Pearson Correlation

Pearson correlation measures the relative shape of the cellular constituent regulations rather than the absolute levels. This is a natural choice because it is widely used to measure cellular constituent correlations. Examples given in Section 6 illustrate the use of Pearson correlation in identifying the most conserved interactions between pair of cellular constituents across five datasets.

5.2.2. Euclidean Distance

Euclidean distance measures the absolute level of cellular constituent regulation, and would not be appropriate for this analysis. For example, two cellular constituents whose abundance levels are matched to one another across the database could still be far apart in Euclidean space if the absolute levels in each experiment are different. The Euclidean distance can also make cellular constituents that are uncorrelated appear close together; for example, if two cellular constituents had abundance levels close to zero across the database but were otherwise randomly correlated they could still appear close in Euclidean space.

5.2.3. Spearman Correlation

The Spearman correlation uses ranks rather than raw expression levels of the cellular constituents, which makes it less sensitive to extreme values in the data. It is possible that extreme values in the dataset will significantly influence the Pearson calculation and thereby enable a small number of microarray experiments to have a disproportionately large effect on our gene similarity measure. Spearman correlations between every pair of cellular constituents may be computed and compared with the results from Pearson correlation calculation. Spearman and Pearson correlation calculations provide convenient methods of cross-validation. However, it has been shown that Pearson correlation more accurately reflects the understand relations between cellular constituents than Spearman correlation does.

5.2.4 Additional Methods for Statistical Analysis

Principal Component Analysis (PCA).

PCA is a technique for simplifying a dataset, by reducing multidimensional datasets to lower dimensions for analysis. PCA is a linear transformation that transforms the data to a new coordinate system such that the greatest variance by any projection of the data comes to lie on the first coordinate (called the first principal component), the second greatest variance on the second coordinate, and so on. PCA can be used for dimensionality reduction in a dataset while retaining those characteristics of the dataset that contribute most to its variance, by keeping lower-order principal components and ignoring higher-order ones. Such low-order components often contain the "most important" aspects of the data. But this is not necessarily the case, depending on the application. PCA has the distinction of being the optimal linear transformation for keeping the subspace that has largest variance. This advantage, however, comes at the price of greater computational requirement if compared, for example, to the discrete cosine transform. Unlike other linear transforms, the PCA does not have a fixed set of basis vectors. Its basis vectors depend on the data set. See Duda et al., 2001, *Pattern Classification*, second edition, John Wiley & Sons, Section 10.13.1, which is hereby incorporated by reference herein in its entirety.

Independent component analysis (ICA). ICA is a computational method for separating a multivariate signal into additive subcomponents supposing the mutual statistical independence of the non-Gaussian source signals. It is a special case of blind source separation. ICA can be divided into noiseless and noisy cases, where noiseless ICA is a special case of noisy ICA. The statistical method finds the independent components (for example, factors, latent variables or sources) by maximizing the statistical independence of the estimated components. Non-Gaussianity, motivated by the central limit theorem, is one method for measuring the independence of the components. Non-Gaussianity can be measured, for instance, by kurtosis or approximations of negentropy. Mutual information is another popular criterion for measuring statistical independence of signals. Typical algorithms for ICA use centering, whitening and dimensionality reduction as preprocessing steps in order to simplify and reduce the complexity of the problem for the actual iterative algorithm. Whitening and dimension reduction can be achieved with principal component analysis or singular value decomposition. Whitening ensures that all dimensions are treated equally a priori before the algorithm is run. Algorithms for ICA include infomax, FastICA and JADE, but there are many others also. See Hyvarinen et al., *Independent Component Analysis*, 2001, John Wiley & Sons, which is hereby incorporated herein by reference.

Canonical Correlation Analysis (CCA).

In statistics, CCA is a way of making sense of cross-covariance matrices. CCA is an additional procedure for assessing the relationship between variables. Specifically, this analysis allows us to investigate the relationship between two sets of variables. For example, an educational researcher may want to compute the (simultaneous) relationship between three measures of scholastic ability with five measures of success in school. A sociologist may want to investigate the relationship between two predictors of social mobility based on interviews, with actual subsequent social mobility as measured by four different indicators. A medical researcher may want to study the relationship of various risk factors to the development of a group of symptoms. In all of these cases, the researcher is interested in the relationship between two sets of variables, and CCA would be the appropriate method of analysis. Some of the computational methods used in canonical correlation analysis include eigenvalues, square root of the eigenvalues, canonical weights and canonical Scores Detailed discussion on PCA, ICA and CCA, may be found in Jolliffe, 2002, *Principal Component Analysis*, Springer; second edition, New York; Hyvärinen, et al., 2001 *Independent Component Analysis*, John Wiley & Sons, New York; Duda et al., 2001, *Pattern Classification*, 570-573, second edition, John Wiley & Sons, New York; Thompson, 1984, *Canonical Correlation Analysis: Uses and Interpretation*, Sage Publications, Inc.; and Cohen and Cohen, 1984, *Applied Multiple Regression/Correlation Analysis for the Behavioral Sciences*, second edition, Lawrence Erlbaum Associates; each of which is hereby incorporated by reference herein in its entirety.

5.3. Exemplary Normalization Routines

A number of different normalization protocols may be used by normalization module 72 to normalize cellular constituent abundance data 44. Some such normalization protocols are described in this Section. Typically, the normalization comprises normalizing the expression level measurement of each cellular constituent in a plurality of cellular constituents that is expressed by an organism in a population of interest. Many of the normalization protocols described in this section are used to normalize microarray data. It will be appreciated that there are many other suitable normalization protocols that may be used in accordance with the present invention. All such protocols are within the scope of the present invention. Many of the normalization protocols found in this section are found in publicly available software, such as Microarray Explorer (Image Processing Section, Laboratory of Experimental and Computational Biology, National Cancer Institute, Frederick, Md. 21702, USA).

One normalization protocol is Z-score of intensity. In this protocol, raw expression intensities are normalized by the (mean intensity)/(standard deviation) of raw intensities for all spots in a sample. For microarray data, the Z-score of intensity method normalizes each hybridized sample by the mean and standard deviation of the raw intensities for all of the spots in that sample. The mean intensity $mnI_i$ and the standard deviation $sdI_i$ are computed for the raw intensity of control genes. It is useful for standardizing the mean (to 0.0) and the range of data between hybridized samples to about −3.0 to +3.0. When using the Z-score, the Z differences ($Z_{diff}$) are computed rather than ratios. The Z-score intensity (Z-score$_{ij}$) for intensity $I_{ij}$ for probe i (hybridization probe, protein, or other binding entity) and spot j is computed as:

$$Z\text{-score}_{ij} = (I_{ij} - mnI_i)/sdI_i,$$

and $$Zdiff_j(x,y) = Z\text{-score}_{xj} - Z\text{-score}_{yj}$$

where x represents the x channel and y represents the y channel.

Another normalization protocol is the median intensity normalization protocol in which the raw intensities for all spots in each sample are normalized by the median of the raw intensities. For microarray data, the median intensity normalization method normalizes each hybridized sample by the median of the raw intensities of control genes (median$I_i$) for all of the spots in that sample. Thus, upon normalization by the median intensity normalization method, the raw intensity $I_{ij}$ for probe i and spot j, has the value $Im_{ij}$ where, $$Im_{ij}=(I_{ij}/\text{median}I_i).$$

Another normalization protocol is the log median intensity protocol. In this protocol, raw expression intensities are normalized by the log of the median scaled raw intensities of representative spots for all spots in the sample. For microarray data, the log median intensity method normalizes each hybridized sample by the log of median scaled raw intensities of control genes (median$I_i$) for all of the spots in that sample. As used herein, control genes are a set of genes that have reproducible accurately measured expression values. The value 1.0 is added to the intensity value to avoid taking the log(0.0) when intensity has zero value. Upon normalization by the median intensity normalization method, the raw intensity $I_{ij}$ for probe i and spot j, has the value $Im_{ij}$ where, $$Im_{ij}=\log(1.0+(I_{ij}/\text{median}I_i)).$$

Yet another normalization protocol is the Z-score standard deviation log of intensity protocol. In this protocol, raw expression intensities are normalized by the mean log intensity (mnL$I_i$) and standard deviation log intensity (sdL$I_i$). For microarray data, the mean log intensity and the standard deviation log intensity is computed for the log of raw intensity of control genes. Then, the Z-score intensity Zlog$S_{ij}$ for probe i and spot j is:

$$Z\log S_{ij}=\{\log(I_{ij})-mnLI_i\}/sdLI_i.$$

Still another normalization protocol is the Z-score mean absolute deviation of log intensity protocol. In this protocol, raw expression intensities are normalized by the Z-score of the log intensity using the equation {log(intensity)−mean logarithm}/standard deviation logarithm. For microarray data, the Z-score mean absolute deviation of log intensity protocol normalizes each bound sample by the mean and mean absolute deviation of the logs of the raw intensities for all of the spots in the sample. The mean log intensity mnL$I_i$ and the mean absolute deviation log intensity madL$I_i$ are computed for the log of raw intensity of control genes. Then, the Z-score intensity $Z \log A_{ij}$ for probe i and spot j is:

$$Z\log A_{ij}=(\log(I_{ij})-mLI_i)/madLI_i.$$

Another normalization protocol is the user normalization gene set protocol. In this protocol, raw expression intensities are normalized by the sum of the genes in a user defined gene set in each sample. This method is useful if a subset of genes has been determined to have relatively constant expression across a set of samples. Yet another normalization protocol is the calibration DNA gene set protocol in which each sample is normalized by the sum of calibration DNA genes. As used herein, calibration DNA genes are genes that produce reproducible expression values that are accurately measured. Such genes tend to have the same expression values on each of several different microarrays. The algorithm is the same as user normalization gene set protocol described above, but the set is predefined as the genes flagged as calibration DNA.

Yet another normalization protocol is the ratio median intensity correction protocol. This protocol is useful in embodiments in which a two-color fluorescence labeling and detection scheme is used. (See, Section 5.7.1.5.). In the case where the two fluors in a two-color fluorescence labeling and detection scheme are Cy3 and Cy5, measurements are normalized by multiplying the ratio (Cy3/Cy5) by medianCy5/medianCy3 intensities. If background correction is enabled, measurements are normalized by multiplying the ratio (Cy3/Cy5) by (medianCy5−medianBkgdCy5)/(medianCy3−medianBkgdCy3) where medianBkgd means median background levels.

In some embodiments, intensity background correction is used to normalize measurements. The background intensity data from a spot quantification programs may be used to correct spot intensity. Background may be specified as either a global value or on a per-spot basis. If the array images have low background, then intensity background correction may not be necessary.

5.4. Diseases and Conditions

In some embodiments of the present invention, the disease or condition under study is a complex trait. The term "complex trait" refers to any clinical trait T that does not exhibit classic Mendelian inheritance. In some embodiments, the term "complex trait" refers to a trait that is affected by two or more gene loci. In some embodiments, the term "complex trait" refers to a trait that is affected by two or more gene loci in addition to one or more factors including, but not limited to, age, sex, habits, and environment. See, for example, Lander and Schork, 1994, Science 265: 2037, which is hereby incorporated by reference herein in its entirety. Such "complex" traits include, but are not limited to, susceptibilities to heart disease, hypertension, diabetes, obesity, cancer, and infection. Complex traits arise when the simple correspondence between genotype and phenotype breaks down, either because the same genotype can result in different phenotypes (due to the effect of chance, environment, or interaction with other genes) or different genotypes can result in the same phenotype.

In some embodiments, a complex trait is one in which there exists no genetic marker that shows perfect cosegregation with the trait due to incomplete penetrance, phenocopy, and/or nongenetic factors (e.g., age, sex, environment, and affect or other genes). Incomplete penetrance means that some individuals who inherit a predisposing allele may not manifest the disease. Phenocopy means that some individuals who inherit no predisposing allele may nonetheless get the disease as a result of environmental or random causes. Thus, the genotype at a given locus may affect the probability of disease, but not fully determine the outcome. The penetrance function $f(G)$, specifying the probability of disease for each genotype G, may also depend on nongenetic factors such as age, sex, environment, and other genes. For example, the risk of breast cancer by ages 40, 55, and 80 is 37%, 66%, and 85% in a woman carrying a mutation at the BCRAI locus as compared with 0.4%, 3%, and 8% in a noncarrier (Easton et al., 1993, Cancer Surv. 18: 1995; Ford et al., 1994, Lancet 343: 692). In such cases, genetic mapping is hampered by the fact that a predisposing allele may be present in some unaffected individuals or absent in some affected individuals.

In some embodiments a complex trait arises because any one of several genes may result in identical phenotypes (genetic heterogeneity). In cases where there is genetic heterogeneity, it may be difficult to determine whether two patients suffer from the same disease for different genetic reasons until the genes are mapped. Examples of complex diseases that arise due to genetic heterogeneity in humans include polycystic kidney disease (Reeders et al., 1987, Human Genetics 76: 348), early-onset Alzheimer's disease (George-Hyslop et al., 1990, Nature 347: 194), maturity-onset diabetes of the young (Barbosa et al., 1976, Diabete Metab. 2: 160), hereditary nonpolyposis colon cancer (Fishel et al., 1993, Cell 75: 1027) ataxia telangiectasia (Jaspers and Bootsma, 1982, Proc. Natl. Acad. Sci. U.S.A. 79: 2641), obesity, non-alcoholic steatohepatitis (NASH) (James & Day, 1998, J. Hepatol. 29: 495-501), nonalcoholic fatty liver (NAFL) (Younossi, et al., 2002, Hepatology 35, 746-752), and xeroderma pigmentosum (De Weerd-Kastelein, Nat. New Biol. 238: 80). Genetic heterogeneity hampers genetic mapping, because a chromosomal region may cosegregate with a disease in some families but not in others.

In still other embodiments, a complex trait arises due to the phenomenon of polygenic inheritance. Polygenic inheritance arises when a trait requires the simultaneous presence of mutations in multiple genes. An example of polygenic inheritance in humans is one form of retinitis pigmentosa, which requires the presence of heterozygous mutations at the peripherin/RDS and ROM1 genes (Kajiwara et al., 1994, Science 264: 1604). It is believed that the proteins coded by RDS and ROM1 are thought to interact in the photoreceptor outer pigment disc membranes. Polygenic inheritance complicates genetic mapping, because no single locus is strictly required to produce a discrete trait or a high value of a quantitative trait.

In yet other embodiments, a complex trait arises due to a high frequency of disease-causing allele "D." A high frequency of disease-causing allele will cause difficulties in mapping even a simple trait if the disease-causing allele occurs at high frequency in the population. That is because the expected Mendelian inheritance pattern of disease will be confounded by the problem that multiple independent copies of D may be segregating in the pedigree and that some individuals may be homozygous for D, in which case one will not observe linkage between D and a specific allele at a nearby genetic marker, because either of the two homologous chromosomes could be passed to an affected offspring. Late-onset Alzheimer's disease provides one example of the problems raised by high frequency disease-causing alleles. Initial linkage studies found weak evidence of linkage to chromosome 19q, but they were dismissed by many observers because the lod score (logarithm of the likelihood ratio for linkage) remained relatively low, and it was difficult to pinpoint the linkage with any precision (Pericak-Vance et al., 1991, Am J. Hum. Genet. 48: 1034). The confusion was finally resolved with the discovery that the apolipoprotein E type 4 allele appears to be the major causative factor on chromosome 19. The high frequency of the allele (16% in most populations) had interfered with the traditional linkage analysis (Corder et al., 1993, Science 261: 921). High frequency of disease-causing alleles becomes an even greater problem if genetic heterogeneity is present.

5.5. Clustering Techniques

The subsections below describe exemplary methods for clustering cellular constituent abundance data. More information on clustering techniques can be found in Kaufman and Rousseeuw, 1990, Finding Groups in Data: An Introduction to Cluster Analysis, Wiley, New York, N.Y.; Everitt, 1993, Cluster analysis (3d ed.), Wiley, New York, N.Y.; Backer, 1995, Computer-Assisted Reasoning in Cluster Analysis, Prentice Hall, Upper Saddle River, N.J.; and Duda et al., 2001, Pattern Classification, John Wiley & Sons, New York, N.Y., each of which is hereby incorporated by reference herein in its entirety.

5.5.1. Hierarchical Clustering Techniques

Hierarchical cluster analysis is a statistical method for finding relatively homogenous clusters of elements based on measured characteristics. Consider a sequence of partitions of n samples into c clusters. The first of these is a partition into n clusters, each cluster containing exactly one sample. The next is a partition into n−1 clusters, the next is a partition into n−2, and so on until the $n^{th}$, in which all the samples form one cluster. Level k in the sequence of partitions occurs when c=n−k+1. Thus, level one corresponds to n clusters and level n corresponds to one cluster. Given any two samples x and x*, at some level they will be grouped together in the same cluster. If the sequence has the property that whenever two samples are in the same cluster at level k they remain together at all higher levels, then the sequence is said to be a hierarchical clustering. Duda et al., 2001, Pattern Classification, John Wiley & Sons, New York, p. 551, which is hereby incorporated herein by reference in its entirety.

5.5.1.1. Agglomerative Clustering

In some embodiments, the hierarchical clustering technique used to cluster QTL vectors and/or gene expression vectors is an agglomerative clustering procedure. Agglomerative (bottom-up clustering) procedures start with n singleton clusters and form a sequence of partitions by successively merging clusters. The major steps in agglomerative clustering are contained in the following procedure, where c is the desired number of final clusters, D, and are clusters, $x_i$ is a QTL vector or gene expression vector, and there are n such vectors:

1  begin intialize $c$, $\hat{c} \leftarrow n$, $D_i \leftarrow \{x_i\}$, $i = 1, \ldots, n$
2         do $\hat{c} \leftarrow \hat{c} - 1$
3              find nearest clusters, say, $D_i$ and $D_j$
4              merge $D_i$ and $D_j$
5         until $c = \hat{c}$
6    return $c$ clusters
7  end In this algorithm, the terminology a←b assigns to variable a the new value b. As described, the procedure terminates when the specified number of clusters has been obtained and returns the clusters as a set of points. A key point in this algorithm is how to measure the distance between two clusters $D_i$ and $D_j$. The method used to define the distance between clusters $D_i$ and $D_j$ defines the type of agglomerative clustering technique used. Representative techniques include the nearest-neighbor algorithm, farthest-neighbor algorithm, the average linkage algorithm, the centroid algorithm, and the sum-of-squares algorithm.

Nearest-Neighbor Algorithm.

The nearest-neighbor algorithm uses the following equation to measure the distances between clusters:

$$d_{min}(D_i, D_j) = \min_{\substack{x \in D_i \\ x' \in D_j}} \|x - x'\|$$

This algorithm is also known as the minimum algorithm. Furthermore, if the algorithm is terminated when the distance between nearest clusters exceeds an arbitrary threshold, it is called the single-linkage algorithm. Consider the case in which the data points are nodes of a graph, with edges forming a path between the nodes in the same subset $D_i$. When dmin( ) is used to measure the distance between subsets, the nearest neighbor nodes determine the nearest subsets. The merging of $D_i$ and $D_j$ corresponds to adding an edge between the nearest pari of nodes in $D_i$ and $D_j$. Because edges linking clusters always go between distinct clusters, the resulting graph never has any closed loops or circuits; in the terminology of graph theory, this procedure generates a tree. If it is allowed to continue until all of the subsets are linked, the result is a spanning tree. A spanning tree is a tree with a path from any node to any other node. Moreover, it can be shown that the sum of the edge lengths of the resulting tree will not exceed the sum of the edge lengths for any other spanning tree for that set of samples. Thus, with the use of dmin( ) as the distance measure, the agglomerative clustering procedure becomes an algorithm for generating a minimal spanning tree. See Duda et al., 2001, *Pattern Classification*, John Wiley & Sons, New York, pp. 553-554, which is hereby incorporated herein by reference in its entirety.

Farthest-Neighbor Algorithm.

The farthest-neighbor algorithm uses the following equation to measure the distances between clusters:

$$d_{max}(D_i, D_j) = \max_{\substack{x \in D_i \\ x' \in D_j}} \|x - x'\|$$

This algorithm is also known as the maximum algorithm. If the clustering is terminated when the distance between the nearest clusters exceeds an arbitrary threshold, it is called the complete-linkage algorithm. The farthest-neighbor algorithm discourages the growth of elongated clusters. Application of this procedure can be thought of as producing a graph in which the edges connect all of the nodes in a cluster. In the terminology of graph theory, every cluster contains a complete subgraph. The distance between two clusters is terminated by the most distant nodes in the two clusters. When the nearest clusters are merged, the graph is changed by adding edges between every pair of nodes in the two clusters.

Average Linkage Algorithm.

Another agglomerative clustering technique is the average linkage algorithm. The average linkage algorithm uses the following equation to measure the distances between clusters:

$$d_{avg}(D_i, D_j) = \frac{1}{n_i n_j} \sum_{x \in D_i} \sum_{x' \in D_j} \|x - x'\|$$

Hierarchical cluster analysis begins by making a pair-wise comparison of all QTL vectors or gene expression vectors in a set of quantitative trait locus vectors or gene expression vectors. After evaluating similarities from all pairs of elements in the set, a distance matrix is constructed. In the distance matrix, a pair of vectors with the shortest distance (i.e. most similar values) is selected. Then, when the average linkage algorithm is used, a "node" ("cluster") is constructed by averaging the two vectors. The similarity matrix is updated with the new "node" ("cluster") replacing the two joined elements, and the process is repeated n−1 times until only a single element remains. Consider six elements, A-F having the values:

A{4.9}, B{8.2}, C{3.0}, D{5.2}, E{8.3}, F{2.3}.

In the first partition, using the average linkage algorithm, one matrix (sol. 1) that could be computed is:

(sol. 1) A {4.9}, B-E{8.25}, C{3.0}, D{5.2}, F{2.3}.

Alternatively, the first partition using the average linkage algorithm could yield the matrix:

(sol. 2) A {4.9}, C{3.0}, D{5.2}, E-B{8.25}, F{2.3}.

Assuming that solution 1 was identified in the first partition, the second partition using the average linkage algorithm will yield:

(sol. 1-1) A-D{5.05}, B-E{8.25}, C{3.0}, F{2.3} or (sol. 1-2) B-E{8.25}, C{3.0}, D-A{5.05}, F{2.3}.

Assuming that solution 2 was identified in the first partition, the second partition of the average linkage algorithm will yield:

(sol. 2-1) A-D{5.05}, C{3.0}, E-B{8.25}, F{2.3} or (sol. 2-2) C{3.0}, D-A{5.05}, E-B{8.25}, F{2.3}.

Thus, after just two partitions in the average linkage algorithm, there are already four matrices. See Duda et al., 2001, *Pattern Classification*, John Wiley & Sons, New York, p. 551, which is hereby incorporated by reference herein in its entirety.

Centroid Algorithm.

In the centroid method, the distances or similarities are calculated between the centroids of the clusters D.

Sum-of-Squares Algorithm.

The sum of squares method is also known as the "Wards' method." In the Wards' method, cluster membership is assessed by calculating the total sum of squared deviations from the mean of a cluster. See Lance and Williams, 1967, Computer Journal 9: 373-380, which is hereby incorporated by reference herein in its entirety, for a general theory of classificatory sorting strategies.

5.5.1.2. Clustering with Pearson Correlation Coefficients

In one embodiment of the present invention, cellular constituent abundance data is clustered using agglomerative hierarchical clustering with Pearson correlation coefficients. In this form of clustering, similarity is determined using Pearson correlation coefficients between the QTL vectors pairs or gene expression pairs. Other metrics that can be used, in addition to the Pearson correlation coefficient, include but are not limited to, a Euclidean distance, a squared Euclidean distance, a Euclidean sum of squares, a Manhattan metric, and a squared Pearson correlation coefficient. Such metrics may be computed using SAS (Statistics Analysis Systems Institute, Cary, N.C.) or S-Plus (Statistical Sciences, Inc., Seattle, Wash.).

5.5.1.3. Divisive Clustering

In some embodiments, the hierarchical clustering technique used to cluster cellular constituent abundance data is a divisive clustering procedure. Divisive (top-down clustering) procedures start with all of the samples in one cluster and form the sequence by successfully splitting clusters. Divisive clustering techniques are classified as either a polythetic or a monthetic method. A polythetic approach divides clusters into arbitrary subsets.

5.5.2. K-Means Clustering

In k-means clustering, cellular constituents in a plurality of cellular constituents are randomly assigned to K user specified clusters. The centroid of each cluster is computed by averaging the value of the vectors in each cluster. Then, for each i=1, . . . , N, the distance between vector $x_i$ and each of the cluster centroids is computed. Each vector $x_i$ is then reassigned to the cluster with the closest centroid. Next, the centroid of each affected cluster is recalculated. The process iterates until no more reassignments are made. See Duda et al., 2001, *Pattern Classification*, John Wiley & Sons, New York, pp. 526-528, which is hereby incorporated herein by reference in its entirety. A related approach is the fuzzy k-means clustering algorithm, which is also known as the fuzzy c-means algorithm. In the fuzzy k-means clustering algorithm, the assumption that every QTL vectors and/or gene expression vector is in exactly one cluster at any given time is relaxed so that every vector has some graded or "fuzzy" membership in a cluster. See Duda et al., 2001, *Pattern Classification*, John Wiley & Sons, New York, pp. 528-530, which is hereby incorporated herein by reference in its entirety.

5.5.3. Jarvis-Patrick Clustering

Jarvis-Patrick clustering is a nearest-neighbor non-hierarchical clustering method in which a set of objects is partitioned into clusters on the basis of the number of shared nearest-neighbors. In the standard implementation advocated by Jarvis and Patrick, 1973, *IEEE Trans. Comput.*, C-22: 1025-1034, which is hereby incorporated herein by reference in its entirety, a preprocessing stage identifies the K nearest-neighbors of each object in the dataset. In the subsequent clustering stage, two objects i and j join the same cluster if (i) i is one of the K nearest-neighbors of j, (ii) j is one of the K nearest-neighbors of i, and (iii) i and j have at least $k_{min}$ of their K nearest-neighbors in common, where K and are user-defined parameters. The method has been widely applied to clustering chemical structures on the basis of fragment descriptors and has the advantage of being much less computationally demanding than hierarchical methods, and thus more suitable for large databases. Jarvis-Patrick clustering may be performed using the Jarvis-Patrick Clustering Package 3.0 (Barnard Chemical Information, Ltd., Sheffield, United Kingdom), which is hereby incorporated herein by reference in its entirety.

5.5.4. Neural Networks

A neural network has a layered structure that includes a layer of input units (and the bias) connected by a layer of weights to a layer of output units. In multilayer neural networks, there are input units, hidden units, and output units. In fact, any function from input to output can be implemented as a three-layer network. In such networks, the weights are set based on training patterns and the desired output. One method for supervised training of multilayer neural networks is back-propagation. Back-propagation allows for the calculation of an effective error for each hidden unit, and thus derivation of a learning rule for the input-to-hidden weights of the neural network.

The basic approach to the use of neural networks is to start with an untrained network, present a training pattern to the input layer, and pass signals through the net and determine the output at the output layer. These outputs are then compared to the target values; any difference corresponds to an error. This error or criterion function is some scalar function of the weights and is minimized when the network outputs match the desired outputs. Thus, the weights are adjusted to reduce this measure of error. Three commonly used training protocols are stochastic, batch, and on-line. In stochastic training, patterns are chosen randomly from the training set and the network weights are updated for each pattern presentation. Multilayer nonlinear networks trained by gradient descent methods such as stochastic back-propagation perform a maximum-likelihood estimation of the weight values in the model defined by the network topology. In batch training, all patterns are presented to the network before learning takes place. Typically, in batch training, several passes are made through the training data. In online training, each pattern is presented once and only once to the net.

5.5.5. Self-Organizing Maps

A self-organizing map is a neural-network that is based on a divisive clustering approach. The aim is to assign cellular constituents to a series of partitions on the basis of the similarity of their expression vectors to reference vectors that are defined for each partition. Consider the case in which there are two microarrays from two different experiments. It is possible to build up a two-dimensional construct where every spot corresponds to the expression levels of any given gene in the two experiments. A two-dimensional grid is built, resulting in several partitions of the two-dimensional construct. Next, a gene is randomly picked and the identity of the reference vector (node) closest to the gene picked is determined based on a distance matrix. The reference vector is then adjusted so that it is more similar to the vector of the assigned gene. That means the reference vector is moved one distance unit on the x axis and y-axis and becomes closer to the assigned gene. The other nodes are all adjusted to the assigned gene, but only are moved one half or one-fourth distance unit. This cycle is repeated hundreds of thousands times to converge the reference vector to fixed value and where the grid is stable. At that time, every reference vector is the center of a group of genes. Finally, the genes are mapped to the relevant partitions depending on the reference vector to which they are most similar.

5.6. Analytic Kit Implementation

The present invention can be implemented as a computer program product that comprises a computer program mechanism embedded in a computer readable storage medium. Further, any of the methods of the present invention can be implemented in one or more computers. Further still, any of the methods of the present invention can be implemented in one or more computer program products. Some embodiments of the present invention provide a computer program product that encodes any or all of the methods disclosed herein. Such methods can be stored on a CD-ROM, DVD, magnetic disk storage product, or any other computer readable data or program storage product. Such methods can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. Such methods encoded in the computer program product can also be distributed electronically, via the Internet or otherwise, by transmission of a computer data signal (in which the software modules are embedded) either digitally or on a carrier wave.

Some embodiments of the present invention provide a computer program product that contains any or all of the program modules shown in FIG. 1. These program modules can be stored on a CD-ROM, DVD, magnetic disk storage product, or any other computer readable data or program storage product. The program modules can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. The software modules in the computer program product can also be distributed electronically, via the Internet or otherwise, by transmission of a computer data signal (in which the software modules are embedded) either digitally or on a carrier wave.

In some embodiment, the methods of this invention can be implemented by use of kits for determining the responses or state of a biological sample. Such kits contain microarrays, such as those described herein. The microarrays contained in such kits comprise a solid phase, e.g., a surface, to which probes are hybridized or bound at a known location of the solid phase. Preferably, these probes consist of nucleic acids of known, different sequence, with each nucleic acid being capable of hybridizing to an RNA species or to a cDNA species derived therefrom. In a particular embodiment, the probes contained in the kits of this invention are nucleic acids capable of hybridizing specifically to nucleic acid sequences derived from RNA species in cells collected from an organism of interest.

In a preferred embodiment, a kit of the invention also contains one or more databases described above and in FIG. 1, encoded on computer readable medium, and/or an access authorization to use the databases described above from a remote networked computer. In another preferred embodiment, a kit of the invention further contains software capable of being loaded into the memory of a computer system such as the one described supra, and illustrated in FIG. 1. The software contained in the kit of this invention, is essentially identical to the software described above in conjunction with FIG. 1. Alternative kits for implementing the analytic methods of this invention will be apparent to one of skill in the art and are intended to be comprehended within the accompanying claims.

5.7. Methods for Measuring Cellular Constituent Abundance

This invention utilizes the ability to measure the abundance of cellular constituents in each organism in a plurality of organisms. This section provides some exemplary methods for measuring the abundance level of cellular constituents. One of skill in the art will appreciate that this invention is not limited to the following specific methods for measuring the abundance level of cellular constituents in each organism in a plurality of organisms.

5.7.1. Transcript Assay Using Microarrays

The techniques described in this section are particularly useful for the determination of the expression state or the transcriptional state of a cell or cell type or any other cell sample by measuring or obtaining expression profiles. Such techniques are used, for example, in some implementations of step 202 described in Section 5.1 These techniques include the provision of polynucleotide probe arrays that can be used to provide simultaneous determination of the expression levels of a plurality of genes. These techniques further provide methods for designing and making such polynucleotide probe arrays.

The expression level of a nucleotide sequence in a gene can be measured by any high throughput technique. However measured, the result is either the absolute or relative amounts of transcripts or response data, including but not limited to values representing abundances or abundance ratios. Preferably, measurement of the expression profile is made by hybridization to transcript arrays, which is described in this subsection. In one embodiment, "transcript arrays" or "profiling arrays" are used. Transcript arrays can be employed for analyzing the expression profile in a cell sample and especially for measuring the expression profile of a cell sample of a particular tissue type or developmental state or exposed to a drug of interest.

In one embodiment, an expression profile is obtained by hybridizing detectably labeled polynucleotides representing the nucleic acid sequences in mRNA transcripts present in a cell (e.g., fluorescently labeled cDNA synthesized from total cell mRNA) to a microarray. A microarray is an array of positionally-addressable binding (e.g., hybridization) sites on a support for representing many of the nucleic acid sequences in the genome of a cell or organism, preferably most or almost all of the genes. Each of such binding sites consists of nucleic acid probe bound to the predetermined region on the support. Microarrays are reproducible, allowing multiple copies of a given array to be produced and compared with each other. Preferably, microarrays are made from materials that are stable under binding (e.g., nucleic acid hybridization) conditions. Preferably, a given binding site or unique set of binding sites in the microarray will specifically bind (e.g., hybridize) to a nucleic acid sequence in a single gene from a cell or organism (e.g., to exon of a specific mRNA or a specific cDNA derived therefrom).

The microarrays used can include one or more test probes, each of which has a nucleic acid sequence that is complementary to a subsequence of RNA or DNA to be detected. Each probe typically has a different nucleic acid sequence, and the position of each probe on the solid surface of the array is usually known. Indeed, the microarrays are preferably addressable arrays, more preferably positionally addressable arrays. Each probe of the array is preferably located at a known, predetermined position on the solid support so that the identity (e.g., the sequence) of each probe can be determined from its position on the array (e.g., on the support or surface). In some embodiments, the arrays are ordered arrays.

Preferably, the density of probes on a microarray or a set of microarrays is 100 different (e.g., non-identical) probes per 1 $cm^2$ or higher. More preferably, a microarray used in the methods of the invention will have at least 550 probes per 1 $cm^2$, at least 1,000 probes per 1 $cm^2$, at least 1,500 probes per 1 $cm^2$ or at least 4,000 probes per 1 $cm^2$. In a particularly preferred embodiment, the microarray is a high density array, preferably having a density of at least 2,500 different probes per 1 $cm^2$. The microarrays used in the invention therefore preferably contain at least 10, at least 100, at least 500, at least 1000, at least 2,500, at least 5,000, at least 10,000, at least 15,000, at least 20,000, at least 25,000, at least 50,000 or at least 55,000 different (e.g., non-identical) probes.

In one embodiment, the microarray is an array (e.g., a matrix) in which each position represents a discrete binding site for a nucleic acid sequence of a transcript encoded by a gene (e.g., for an exon of an mRNA or a cDNA derived therefrom). The array of binding sites on a microarray contains sets of binding sites for a plurality of genes. For example, in various embodiments, the microarrays of the invention can comprise binding sites for products encoded by fewer than 5% of the genes in the genome of an organism. Alternatively, the microarrays of the invention can have binding sites for the products encoded by at least 5%, at least 10%, at least 25%, at least 50%, at least 75%, at least 85%, at least 90%, at least 95%, at least 99% or 100% of the genes in the genome of an organism. In other embodiments, the microarrays of the invention can having binding sites for products encoded by fewer than 50%, by at least 50%, by at least 75%, by at least 85%, by at least 90%, by at least 95%, by at least 99% or by 100% of the genes expressed by a cell of an organism. The binding site can be a DNA or DNA analog to which a particular RNA can specifically hybridize. The DNA or DNA analog can be, e.g., a synthetic oligomer or a gene fragment, e.g. corresponding to an exon.

In some embodiments, a gene or an exon in a gene is represented in the microarrays by a set of binding sites comprising probes with different polynucleotides that are complementary to different sequence segments of the gene or the exon. Such polynucleotides are preferably of the length of 15 to 200 bases, more preferably of the length of 20 to 100 bases, most preferably 40-60 bases. Each probe sequence may also comprise linker sequences in addition to the sequence that is complementary to its target sequence. As used herein, a linker sequence is a sequence between the sequence that is complementary to its target sequence and the surface of support. In some instances, a microarray comprises one probe specific to each target gene or gene fragment. However, if desired, a microarray may contain at least 2, 5, 10, 100, or 1000 or more probes specific to some target genes under study. For example, the microarray may contain probes tiled across the sequence of the longest mRNA isoform of a gene at single base steps.

In specific embodiments of the invention, when an exon has alternative spliced variants, a set of nucleic acid probes of successive overlapping sequences, e.g., tiled sequences, across the genomic region containing the longest variant of an exon can be included in the microarray. The set of nucleic acid probes can comprise successive overlapping sequences at steps of a predetermined base intervals, e.g. at steps of 1, 5, or 10 base intervals, span, or are tiled across, the mRNA containing the longest variant. Such sets of nucleic acid probes therefore can be used to scan the genomic region containing all variants of a gene to determine the expressed variant or variants of the gene to determine the expressed variant or variants of the gene. Alternatively or additionally, a set of nucleic acid probes comprising gene specific probes and/or variant junction probes can be included in the microarray.

In some cases, a gene is represented in the microarray by a probe comprising a nucleic acid that is complementary to a portion of the full length gene. In some instances, a gene is represented by a single binding site on the profiling arrays. In some instance, a gene is represented by one or more binding sites on the microarray, each of the binding sites comprising a probe with a nucleic acid sequence that is complementary to an RNA fragment that is a portion of the target gene. The lengths of such probes are normally between 15-600 bases, preferably between 20-200 bases, more preferably between 30-100 bases, and most preferably between 40-80 bases. A probe of length 40-80 allows more specific binding of the gene than a probe of shorter length, thereby increasing the specificity of the probe to the target gene.

It will be apparent to one skilled in the art that any of the probe schemes, supra, can be combined on the same microarray and/or on different microarray within the same set of microarrays so that a more accurate determination of the expression profile for a plurality of genes (or cellular constituents) can be accomplished. It will also be apparent to one skilled in the art that the different probe schemes can also be used for different levels of accuracies in profiling. For example, a microarray comprising a small set of probes for each gene may be used to determine the relevant genes and/or RNA splicing pathways under certain specific conditions. A microarray or microarray set comprising larger sets of probes for the genes that are of interest is then used to more accurately determine the gene expression profile under such specific conditions. Other microarray strategies that allow more advantageous use of different probe schemes are also encompassed by the present invention.

It will be appreciated that when cDNA complementary to the RNA of a cell is made and hybridized to a microarray under suitable hybridization conditions, the level of hybridization to the site in the array corresponding to a particular gene will reflect the prevalence in the cell of mRNA or mRNAs containing the mRNA transcribed from that gene. For example, when detectably labeled (e.g., with a fluorophore) cDNA complementary to the total cellular mRNA is hybridized to a microarray, the site on the array corresponding to a gene (e.g., capable of specifically binding the product or products of the gene expressing) that is not transcribed or is removed during RNA splicing in the cell will have little or no signal (e.g., fluorescent signal), and a gene for which the encoded mRNA expressing the gene is prevalent will have a relatively strong signal.

5.7.1.1. Preparing Probes for Microarrays

As noted above, the "probe" to which a particular polynucleotide molecule, such as an exon, specifically hybridizes according to the invention is a complementary polynucleotide sequence. Preferably one or more probes are selected for each target gene. For example, when a minimum number of probes are to be used for the detection of a gene, the probes normally comprise nucleotide sequences greater than 40 bases in length. Alternatively, when a large set of redundant probes is to be used for a gene, the probes normally comprise nucleic acid sequences of 40-60 bases. The probes can also comprise sequences complementary to full length exons. It will be understood that each probe sequence can also comprise linker sequences in addition to the sequence that is complementary to its target sequence.

The probes may comprise DNA or DNA "mimics" (e.g., derivatives and analogs) corresponding to a portion of each gene in an organism's genome. In one embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates. DNA can be obtained, e.g., by polymerase chain reaction (PCR) amplification of gene segments from genomic DNA, cDNA (e.g., by RT-PCR), or cloned sequences. PCR primers are preferably chosen based on known sequence of the genes or cDNA that result in amplification of unique fragments (e.g., fragments that do not share more than 10 bases of contiguous identical sequence with any other fragment on the microarray). Computer programs that are well known in the art are useful in the design of primers with the required specificity and optimal amplification properties, such as Oligo version 5.0 (National Biosciences). Typically each probe on the microarray will be between 20 bases and 600 bases, and usually between 30 and 200 bases in length. PCR methods are well known in the art, and are described, for example, in Innis et al., eds., 1990, *PCR Protocols: A Guide to Methods and Applications*, Academic Press Inc., San Diego, Calif. It will be apparent to one skilled in the art that controlled robotic systems are useful for isolating and amplifying nucleic acids.

An alternative, preferred means for generating the nucleic acid probes of the microarray is by synthesis of synthetic polynucleotides or oligonucleotides, e.g., using N-phosphonate or phosphoramidite chemistries. See, for example, Froehler et al., 1986, *Nucleic Acid Res.* 14:5399-5407; and McBride et al., 1983, *Tetrahedron Lett.* 24:246-248, each of which is hereby incorporated by reference herein in its entirety. Synthetic sequences are typically between 15 and 600 bases in length, more typically between 20 and 100 bases, most preferably between 40 and 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid. See, e.g., Egholm et al., 1993, *Nature* 363:566-568; and U.S. Pat. No. 5,539,083, each of which is hereby incorporated herein by reference in its entirety. In alternative embodiments, the hybridization sites (e.g., the probes) are made from plasmid or phage clones of genes, cDNAs (e.g., expressed sequence tags), or inserts therefrom (Nguyen et al., 1995, *Genomics* 29:207-209).

5.7.1.2. Attaching Nucleic Acids to the Solid Surface

There are two main approaches used for microarray fabrication: deposition of nucleic acid fragments and in situ synthesis. The first type of fabrication involves two methods: deposition of PCR-amplified cDNA clones and printing of already synthesized nucleic acids. In situ manufacturing can be divided into photolithography, ink jet printing and electrochemical analysis. See for example, Draghici, 2003, *Data Analysis Tools for DNA Microarrays*, pp. 16-22, which is hereby incorporated by reference herein in its entirety.

In the deposition fabrication approach, microarray probes are attached to a solid support or surface, which may be made, e.g., from glass, plastic (e.g., polypropylene, nylon), polyacrylamide, nitrocellulose, gel, or other porous or nonporous material. One method for attaching the nucleic acids to a surface is by printing on glass plates, as is described generally by Schena et al., 1995, *Science* 270:467-470. This method is useful for preparing microarrays of cDNA (See also, DeRisi et al., 1996, *Nature Genetics* 14:457-460; Shalon et al., 1996, *Genome Res.* 6:639-645; and Schena et al., 1995, *Proc. Natl. Acad. Sci. U.S.A.* 93:10539-11286).

Another method for making microarrays is by making high-density polynucleotide arrays. Techniques are known for producing arrays containing thousands of nucleic acids complementary to defined sequences, at defined locations on a surface using photolithographic techniques for synthesis in situ (see, Fodor et al., 1991, *Science* 251:767-773; Lockhart et al., 1996, *Nature Biotechnology* 14:1675; U.S. Pat. Nos. 5,578,832; 5,556,752; and 5,510,270) or other methods for rapid synthesis and deposition of defined nucleic acids (Blanchard et al., *Biosensors & Bioelectronics* 11:687-690). When these methods are used, nucleic acids (e.g., 60-mers) of known sequence are synthesized directly on a surface such as a derivatized glass slide. The array produced can be redundant, with several polynucleic acid molecules per exon.

Other methods for making microarrays, e.g., by masking (Maskos and Southern, 1992, *Nucl. Acids. Res.* 20:1679-1684), can also be used. In principle, and as noted supra, any type of array, for example, dot blots on a nylon hybridization membrane (see Sambrook et al., supra) could be used. However, as will be recognized by those skilled in the art, very small arrays will frequently be preferred because hybridization volumes will be smaller.

In one embodiment, a microarray is manufactured by means of an ink jet printing device for nucleic acid synthesis, e.g., using the methods and systems described by Blanchard in International Patent Publication No. WO 98/41531, published Sep. 24, 1998; Blanchard et al., 1996, *Biosensors and Bioelectronics* 11:687-690; Blanchard, 1998, in *Synthetic DNA Arrays in Genetic Engineering* 20, Setlow, Ed., Plenum Press, New York at pages 111-123; and U.S. Pat. No. 6,028,189 to Blanchard. Specifically, the nucleic acid probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (e.g., the different probes). Polynucleic acid probes are normally attached to the surface covalently at the 3' end of the polynucleic acid. Alternatively, polynucleic acid probes can be attached to the surface covalently at the 5' end of the nucleic acid (see for example, Blanchard, 1998, in *Synthetic DNA Arrays in Genetic Engineering* 20, Setlow, Ed., Plenum Press, New York at pages 111-123).

5.7.1.3. Target Polynucleotide Molecules

Target polynucleotides that can be measured to obtain cellular constituent abundance data include, but are not limited to, RNA molecules such as, but by no means limited to, messenger RNA (mRNA) molecules, ribosomal RNA (rRNA) molecules, cRNA molecules (e.g., RNA molecules prepared from cDNA molecules that are transcribed in vivo) and fragments thereof. Other target polynucleotides which may also be measured to obtain cellular constituent abundance data include, but are not limited to DNA molecules such as genomic DNA molecules, cDNA molecules, and fragments thereof including oligonucleotides, ESTs, STSs, etc.

The target polynucleic acids can be from any source. For example, the target polynucleic acids may be naturally occurring nucleic acid molecules such as genomic or extragenomic DNA molecules isolated from an organism, or RNA molecules, such as mRNA molecules, isolated from an organism. Alternatively, the polynucleic acids may be synthesized, including, e.g., nucleic acid molecules synthesized enzymatically in vivo or in vitro, such as cDNA molecules, or polynucleotide molecules synthesized by PCR, RNA molecules synthesized by in vitro transcription, etc. The sample of target polynucleic acids can comprise, e.g., molecules of DNA, RNA, or copolymers of DNA and RNA. In preferred embodiments, the target polynucleic acids of the invention will correspond to particular genes or to particular gene transcripts (e.g., to particular mRNA sequences expressed in cells or to particular cDNA sequences derived from such mRNA sequences). However, in many embodiments, particularly those embodiments in which the polynucleic acids are derived from mammalian cells, the target polynucleic acids may correspond to particular fragments of a gene transcript. For example, the target polynucleic acids may correspond to different variants of the same gene, e.g., so that different splice variants of that gene may be detected and/or analyzed.

In some embodiments, the target polynucleic acids to be measured to obtain cellular constituent abundance data are prepared in vitro from nucleic acids extracted from cells. For example, in one embodiment, RNA is extracted from cells (e.g., total cellular RNA, poly(A)$^+$ messenger RNA, fraction thereof) and messenger RNA is purified from the total extracted RNA. Methods for preparing total and poly(A)$^+$ RNA are well known in the art, and are described generally, e.g., in Sambrook et al., supra. In one embodiment, RNA is extracted from cells of the various types of interest in this invention using guanidinium thiocyanate lysis followed by CsCl centrifugation and an oligo dT purification (Chirgwin et al., 1979, *Biochemistry* 18:5294-5299). In another embodiment, RNA is extracted from cells using guanidinium thiocyanate lysis followed by purification on RNeasy columns (Qiagen). cDNA is then synthesized from the purified mRNA using, e.g., oligo-dT or random primers. In some embodiments, the target polynucleic acids are cRNA prepared from purified messenger RNA extracted from cells. As used herein, cRNA is defined here as RNA complementary to the source RNA. The extracted RNAs are amplified using a process in which doubled-stranded cDNAs are synthesized from the RNAs using a primer linked to an RNA polymerase promoter in a direction capable of directing transcription of anti-sense RNA. Anti-sense RNAs or cRNAs are then transcribed from the second strand of the double-stranded cDNAs using an RNA polymerase (see, e.g., U.S. Pat. Nos. 5,891,636, 5,716,785; 5,545,522 and 6,132,997; see also, U.S. Pat. No. 6,271,002, and U.S. Provisional Patent Application Ser. No. 60/253,641, filed on Nov. 28, 2000, by Ziman et al.). Both oligo-dT primers (U.S. Pat. Nos. 5,545,522 and 6,132,997) or random primers (U.S. Provisional Patent Application Ser. No. 60/253,641, filed on Nov. 28, 2000, by Ziman et al.) that contain an RNA polymerase promoter or complement thereof can be used. Preferably, the target polynucleic acids are short and/or fragmented polynucleic acids which are representative of the original nucleic acid population of the cell.

The target polynucleic acids to be measured to obtain cellular constituent abundance data are detectably labeled in some embodiments. For example, cDNA can be labeled directly, e.g., with nucleotide analogs, or indirectly, e.g., by making a second, labeled cDNA strand using the first strand as a template. Alternatively, the double-stranded cDNA can be transcribed into cRNA and labeled. Preferably, the detectable label is a fluorescent label, e.g., by incorporation of nucleotide analogs. Other labels suitable for use include, but are not limited to, biotin, iminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Exemplary suitable radioactive isotopes include $^{32}$P, $^{35}$S, $^{14}$C, $^{15}$N and $^{125}$I. Fluorescent molecules suitable for the present invention include, but are not limited to, fluorescein and its derivatives, rhodamine and its derivatives, texas red, 5' carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6' carboxy-X-rhodamine ("ROX"), HEX, TET, IRD40, and IRD41. Fluorescent molecules that are suitable for the invention further include: cyamine dyes, including by not limited to Cy3, Cy3.5 and Cy5; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold. Alternatively, in some embodiments the target polynucleic acids may be labeled by specifically complexing a first group to the polynucleic acid. A second group, covalently linked to an indicator molecules and which has an affinity for the first group, can be used to indirectly detect the target polynucleic acid. In such an embodiment, compounds suitable for use as a first group include, but are not limited to, biotin and iminobiotin. Compounds suitable for use as a second group include, but are not limited to, avidin and streptavidin.

5.7.1.4. Hybridization to Microarrays

As described supra, nucleic acid hybridization and wash conditions are chosen so that the polynucleic acid molecules to be measured, in order to obtain cellular constituent abundance data, specifically bind or specifically hybridize to the complementary polynucleic acid sequences of the array, preferably to a specific array site in which its complementary DNA is located.

Microarrays containing double-stranded probe DNA situated thereon are preferably subjected to denaturing conditions to render the DNA single-stranded prior to contacting with the target polynucleic acids. Microarrays containing single-stranded nucleic acid probes (e.g., synthetic oligodeoxyribonucleic acids) may need to be denatured prior to contacting with the target polynucleic acids, e.g., to remove hairpins or dimers which form due to self complementary sequences.

Optimal hybridization conditions will depend on the length (e.g., oligomer versus polynucleic acid greater than 200 bases) and type (e.g., RNA, or DNA) of probe and target nucleic acids. As used herein, a polynucleic acid is any nucleic acid that is two bais pairs long or longer (e.g., greater than 5 base pairs, greater than 10 base pairs, greater than 30 base pairs, greater than 50 base pairs, greater than 80 base pairs, etc.). General parameters for specific (e.g., stringent) hybridization conditions for polynucleic acids are described in Sambrook et al., (supra), and in Ausubel et al., 1987, *Current Protocols in Molecular Biology*, Greene Publishing and Wiley-Interscience, New York. When the cDNA microarrays of Schena et al. are used, typical hybridization conditions are hybridization in 5×SSC plus 0.2 percent SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Shena et al., 1996, *Proc. Natl. Acad. Sci. U.S.A.* 93:10614). Useful hybridization conditions are also provided in, e.g., Tijessen, 1993, *Hybridization with Nucleic Acid Probes*, Elsevier Science Publishers B.V. and Kricka, 1992, Nonisotopic DNA Probe Techniques, Academic Press, San Diego, Calif.

Particularly preferred hybridization conditions for use with the screening and/or signaling chips of the present invention include hybridization at a temperature at or near the mean melting temperature of the probes (e.g., within 5° C., more preferably within 2° C.) in 1 M NaCl, 50 mM MES buffer (pH 6.5), 0.5 percent sodium Sarcosine and thirty percent formamide.

5.7.1.5. Signal Detection and Data Analysis

It will be appreciated that when target sequences, e.g., cDNA or cRNA, complementary to the RNA of a cell is made and hybridized to a microarray under suitable hybridization conditions, the level of hybridization to the site in the array corresponding to any particular gene will reflect the prevalence in the cell of mRNA or mRNAs transcribed from that gene. For example, when detectably labeled (e.g., with a fluorophore) cDNA complementary to the total cellular mRNA is hybridized to a microarray, the site on the array for a gene (e.g., capable of specifically binding the product or products of the gene expressing) that is not transcribed will have little or no signal (e.g., fluorescent signal), and a gene for which the encoded mRNA expressing the gene is prevalent will have a relatively strong signal.

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. In some embodiments, the arrays are scanned with a laser fluorescence scanner with a computer controlled X-Y stage and a microscope objective. Excitation of the fluorophores is achieved with a laser, and the emitted light is detected with a photomultiplier tube. Such fluorescence laser scanning devices are described, e.g., in Schena et al., 1996, *Genome Res.* 6:639-645. Alternatively, the fiber-optic bundle described by Ferguson et al., 1996, *Nature Biotech.* 14:1681-1684, may be used to monitor mRNA abundance levels at a large number of sites simultaneously.

Signals are recorded and, in a preferred embodiment, analyzed by computer. In one embodiment, the scanned image is despeckled using a graphics program (e.g., Hijaak Graphics Suite) and then analyzed using an image gridding program that creates a spreadsheet of the average hybridization at each wavelength at each site. More information on image processing of microarrays is provided in Draghici, 2003, *Data Analysis Tools for DNA Microarrays*, pp. 33-59, hereby incorporated by reference herein in its entirety, including spot finding, image segmentation, quantification, and spot quality assessment.

5.7.2. Other Methods of Transcriptional State Measurement

The transcriptional state of a cell may be measured by other gene expression technologies known in the art. Several such technologies produce pools of restriction fragments of limited complexity for electrophoretic analysis, such as methods combining double restriction enzyme digestion with phasing primers (See, e.g., European Patent O 534858 A1, filed Sep. 24, 1992, by Zabeau et al, which is hereby incorporated herein by reference in its entirety), or methods selecting restriction fragments with sites closest to a defined mRNA end (see, e.g., Prashar et al., 1996, *Proc. Natl. Acad. Sci. USA* 93:659-663, which is hereby incorporated herein by reference in its entirety). Other methods statistically sample cDNA pools, such as by sequencing sufficient bases (e.g., 20-50 bases) in each of multiple cDNAs to identify each cDNA, or by sequencing short tags (e.g., 9-10 bases) that are generated at known positions relative to a defined mRNA end (see, e.g., Velculescu, 1995, *Science* 270:484-487, which is hereby incorporated herein by reference in its entirety).

5.7.3. Measurement of Other Aspects of the Biological State

In various embodiments of the present invention, aspects of the biological state other than the transcriptional state, such as the translational state, the activity state, or mixed aspects can be measured to obtain cellular constituent abundance data. Thus, in such embodiments, gene expression data can include translational state measurements or even protein expression measurements. Details of embodiments in which aspects of the biological state other than the transcriptional state are described in this section.

5.7.3.1. Translational State Measurements

Measurement of the translational state can be performed according to several methods. For example, whole genome monitoring of protein (e.g., the "proteome,") can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to the action of a drug of interest. Methods for making monoclonal antibodies are well known (see, e.g., Harlow and Lane, 1988, *Antibodies: A Laboratory Manual*, Cold Spring Harbor, N.Y., which is incorporated in its entirety for all purposes). In one embodiment, monoclonal antibodies are raised against synthetic peptide fragments designed based on genomic sequence of the cell. With such an antibody array, proteins from the cell are contacted to the array and their binding is assayed with assays known in the art.

In some embodiments, cellular constituent measurements are made using a protein chip assay (e.g., The ProteinChip® Biomarker System, Ciphergen, Fremont, Calif.). See also, for example, Lin, 2004, Modern Pathology, 1-9; Li, 2004, Journal of Urology 171, 1782-1787; Wadsworth, 2004, Clinical Cancer Research 10, 1625-1632; Prieto, 2003, Journal of Liquid Chromatography & Related Technologies 26, 2315-2328; Coombes, 2003, Clinical Chemistry 49, 1615-1623; Mian, 2003, Proteomics 3, 1725-1737; Lehre et al., 2003, BJU International 92, 223-225; and Diamond, 2003, Journal of the American Society for Mass Spectrometry 14, 760-765, which are hereby incorporated by reference in their entireties. Protein chip assays (protein microarrays) are commercially available. For example, Ciphergen (Fremont, Calif.) markets the ProteinChip® System Series 4000 for quantifying proteins in a sample. Furthermore, Sigma-Aldrich (Saint Lewis, Mo.) sells a number of protein microarrays including the Panorama™ Human Cancer v1 Protein Array, the Panorama™ Human Kinase v1 Protein Array, the Panorama™ Signal Transduction Functional Protein Array, the Panorama™ AB Microarray—Cell Signaling Kit, the Panorama™ AB Microarray—MAPK and PKC Pathways kit, the Panorama™ AB Microarray—Gene Regulation I Kit, and the Panorama™ AB Microarray—p53 pathways kit. Further, TeleChem International, Inc. (Sunnyvale, Calif.) markets a Colorimetric Protein Microarray Platform that can perform a variety of micro multiplexed protein microarray assays including microarray based multiplex ELISA assays. See also, MacBeath and Schreiber, 2000, "Printing Proteins as Microarrays for High-Throughput Function Determination," Science 289, 1760-1763, which is hereby incorporated by reference herein in its entirety.

Alternatively, proteins can be quantified by first separating them using two-dimensional gel electrophoresis systems. Two-dimensional gel electrophoresis is well-known in the art and typically involves isoelectric focusing along a first dimension followed by SDS-PAGE electrophoresis along a second dimension. See, e.g., Hames et al., 1990, *Gel Electrophoresis of Proteins: A Practical Approach*, IRL Press, New York; Shevchenko et al., 1996, *Proc. Natl. Acad. Sci. USA* 93:1440-1445; Sagliocco et al., 1996, *Yeast* 12:1519-1533;

Lander, 1996, Science 274:536-539. The resulting electropherograms can be analyzed by numerous techniques, including mass spectrometric techniques, Western blotting and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or over-expression of a specific gene.

5.7.3.2. Other Types of Cellular Constituent Abundance Measurements

The methods of the invention are applicable to any cellular constituent that can be measured to obtain cellular constituent abundance data. For example, activities of proteins can be measured to obtain cellular constituent abundance data. Activity measurements can be performed by any functional, biochemical, or physical means appropriate to the particular activity being characterized. Where the activity involves a chemical transformation, the cellular protein can be contacted with the natural substrate(s), and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known and measured, the changes in protein activities form the response data analyzed by the foregoing methods of this invention.

In some embodiments of the present invention, cellular constituent measurements are made using cellular phenotypic techniques in order to obtain cellular constituent abundance data. One such cellular phenotypic technique uses cell respiration as a universal reporter. In one embodiment, 96-well microtiter plate, in which each well contains its own unique chemistry is provided. Each unique chemistry is designed to test a particular phenotype. Cells from the organism of interest are pipetted into each well. If the cells exhibit the appropriate phenotype, they will respire and actively reduce a tetrazolium dye, forming a strong purple color. A weak phenotype results in a lighter color. No color means that the cells don't have the specific phenotype. Color changes can be recorded as often as several times each hour. During one incubation, more than 5,000 phenotypes can be tested. See, for example, Bochner et al., 2001, Genome Research 11, 1246, which is hereby incorporated by reference herein in its entirety.

In some embodiments of the present invention, cellular constituent abundance data is measured using cellular phenotypic techniques. One such cellular phenotypic technique uses cell respiration as a universal reporter. In one embodiment, 96-well microtiter plates, in which each well contains its own unique chemistry is provided. Each unique chemistry is designed to test a particular phenotype. Cells from an organism of interest are pipetted into each well. If the cells exhibit the appropriate phenotype, they will respire and actively reduce a tetrazolium dye, forming a strong purple color. A weak phenotype results in a lighter color. No color means that the cells don't have the specific phenotype. Color changes can be recorded as often as several times each hour. During one incubation, more than 5,000 phenotypes can be tested. See, for example, Bochner et al., 2001, Genome Research 11, 1246-55, which is hereby incorporated by reference herein.

In some embodiments of the present invention, cellular constituent abundance data comprises measurements of metabolites. Metabolites include, but are not limited to, amino acids, metals, soluble sugars, sugar phosphates, and complex carbohydrates. Such metabolites can be measured, for example, at the whole-cell level using methods such as pyrolysis mass spectrometry (Irwin, 1982, *Analytical Pyrolysis: A Comprehensive Guide*, Marcel Dekker, New York; Meuzelaar et al., 1982, *Pyrolysis Mass Spectrometry of Recent and Fossil Biomaterials*, Elsevier, Amsterdam), fourier-transform infrared spectrometry (Griffiths and de Haseth, 1986, *Fourier transform infrared spectrometry*, John Wiley, New York; Helm et al., 1991, J. Gen. Microbiol. 137, 69-79; Naumann et al., 1991, Nature 351, 81-82; Naumann et al., 1991, In: *Modern techniques for rapid microbiological analysis*, 43-96, Nelson, W. H., ed., VCH Publishers, New York), Raman spectrometry, gas chromatography-mass spectroscopy (GC-MS) (Fiehn et al., 2000, Nature Biotechnology 18, 1157-1161, capillary electrophoresis (CE)/MS, high pressure liquid chromatography/mass spectroscopy (HPLC/MS), as well as liquid chromatography (LC)-Electrospray and cap-LC-tandem-electrospray mass spectrometries. Such methods can be combined with established chemometric methods that make use of artificial neural networks and genetic programming in order to discriminate between closely related samples.

6. EXAMPLES

The following examples are presented by way of illustration of the previously described invention and are not limiting of that description. The systems and methods outlined in Section 5.1 as well as FIG. 2 were applied to the abundance data derived from diverse large scale mouse liver gene expression profiling experiments.

6.1 Generating Datasets of Gene Expression Profiling Experiments

In order to determine the conserved interactions between cellular constituents, a diverse mouse liver gene expression experiments was built based on a collection of historic gene expression experiments in a Resolver (Rosetta Inpharmatics) database comprising 1200 experiments across about 20,000 genes. The large dataset was referred to as the MegaEG dataset. Additional datasets were built to include mouse liver gene expression experiments of two independent F2 mouse crosses: the C57BL/6J×C3H ApoE null F2 cross (F2 apoE) and the C57B/6×C3H ApoE wildtype F2 cross (F2 wt). Given the significant gender effects, which were noted in previous analyses, the gene expression data from the each F2 crosses were further separated by gender of the mice into two independent sub-datasets. A total of five large datasets were assembled that included a very diverse set of experimental conditions to the transcriptional network in the mouse liver: MegaED, F2 B×H/apoE Female (i.e., F2 apoE F), F2 B×H/apoE Male (i.e., F2 apoE M), F2 B×H/wt Female (i.e., F2 wt F), and F2 B×H/wt Male (i.e., F2 wt M).

6.2. Data Selection in the Large Scale Datasets

A hypothesis was formulated that only those genes vary significantly across the experimental conditions have greater potential to result in statistically significant gene pair correlations. Approaches were taken to exclude the genes that bear small significance based on the hypothesis. First, a standard deviation was computed for each gene within each dataset over all experimental conditions. Second, the median value of the standard deviations of all genes in a given dataset was also computed. Those genes with standard deviations greater than two times of the median value of the standard deviation were included in the dataset for further study. This selection process was repeated for all five datasets. Third, among the five datasets containing only the genes that had passed the previous selection steps, a set of genes that were commonly present in all five datasets were identified. In the mouse liver gene expression experiments, a set of 233 common genes were identified from the above selection processes. All five datasets were then truncated to contain gene expression data of only those 233 common genes.

6.3. Computing Gene-Gene Correlation Between Datasets

Correlation coefficients were computed as Pearson correlation coefficients of the mean log ratio (mlratio) vectors for all gene pairs of the 233 selected genes in the five truncated datasets. Pearson correlations were calculated either as pairwise correlation coefficient between cellular constituents within the same dataset or as a generalized correlation coefficient between two matrices of pairwise correlation coefficients.

Figure 3:
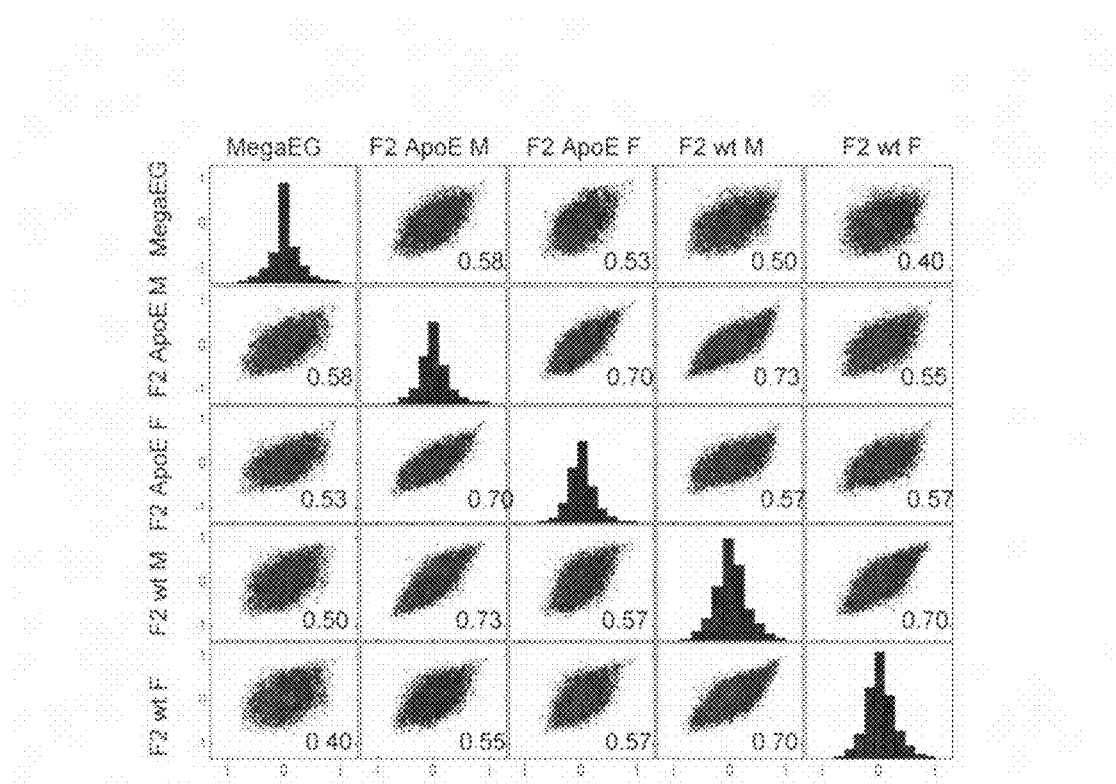
FIG. 3 illustrates the computation of Pearson correlation coefficients using abundance data from a single dataset or using abundance data from two different datasets, in accordance with an embodiment of the present invention.

FIG. 3 illustrates the three ways of computing Pearson correlation coefficients. The histograms in the diagonal grids in FIG. 3 illustrate the distributions of Pearson correlation coefficient values for all gene pairs within a dataset. As shown in the histograms, majority of the gene pairs within an abundance dataset have Pearson correlation coefficients close to zero, which suggests that the majority of the genes within the 233 selected genes do not correlate with each other significantly. It is also interesting to note that the histograms follow a similar distribution pattern. This result indicates that high correlations of the gene pairs are not random and abundant occurrence, which in turn suggests that the stronger interactions between selected gene pairs, especially those conserved across large number of datasets, provides fundamentally important information on the complex cellular gene-gene networks.

The distribution graphs of dots in the non-diagonal grids depict all the Pearson coefficients which were calculated for gene pairs between the respective datasets. Pearson coefficients values fall between −1 and 1. Positive values indicate positive correlation in gene expression levels. Negative values indicate reverse correlation in gene expression levels. A value around zero indicates little or no correlation in gene expression level.

The numbers at the corner of the grids in FIG. 3 represent the general Pearson correlation coefficients calculated for the two corresponding datasets using the correlation coefficients for all gene pairs in each datasets. FIG. 3 shows that when all gene pair correlations (233×233) were compared among five different datasets, there was a clear correlation between these pairs of datasets (e.g., their general correlation coefficients were around or over 0.7). This piece of information was the initial indication that conserved gene-gene interactions were represented across five diverse datasets. As expected, the gene pair correlations were most highly correlated within the same cross. It is also interesting to note that the two male F2 mice datasets (the B×H/apoE and B×H/wt crosses) had a general correlation coefficient value of over 0.7. The general correlation coefficient values between MegaEG and the two F2 crosses were comparable.

6.4. Two-Dimensional Agglomerative Clustering of Gene-Gene Correlation for MegaEG The MegaEG correlation dataset was selected for clustering analysis. In order to apply the two-dimensional agglomerative clustering technique, the correlation coefficients in the MegaEG correlation dataset were rendered into a two-dimensional similarity matrix. The similarity matrix for MegaEG correlation dataset was a two-dimensional correlation grid map formed by two orthogonal axes. Each axis contained 233 units. Every unit corresponded to one of the 233 selected genes in the truncated dataset. The 233 selected genes were arranged in the same order on both axes. As the result of this arrangement, a correlation grid map with 233×233 grids was constructed for each dataset. Each grid on the correlation matrix map corresponded to the correlation value of a gene pair designated by intersecting units from the two axes.

Colors were assigned to correlation grids before the grids were clustered. For example, all the grids with correlation values below −0.6 were assigned the color cyan; and all the grids with correlation values above 0.6 were assigned the color magenta. The grids with correlation values between −0.6 and 0.6 were linearly mapped to the colors that slowly changed from cyan to magenta as correlation increased.

Two-dimensional agglomerative clustering for MegaEG was then performed such that the grids with color corresponding to the same level of correlations (e.g., very strong correlations) were placed adjacent to each other. FIG. 4A illustrates the two-dimensional agglomerative clustering result for the MegaEG dataset. Magenta grids, which correspond to strong gene-gene correlations, were clustered into four distinct groups, i.e., clusters A, B, C, and D. After the clustering process was finished, the order of the gene arrangement on each axis of the two-dimensional grid map was recorded. Because the two-dimensional grid map was initially constructed using two identical but orthogonal axes, the order of gene arrangement on the two axes would remain identical after the clustering process. Furthermore, there was always a two-fold symmetry in the resulting clustering patterns.

Figure 4B:
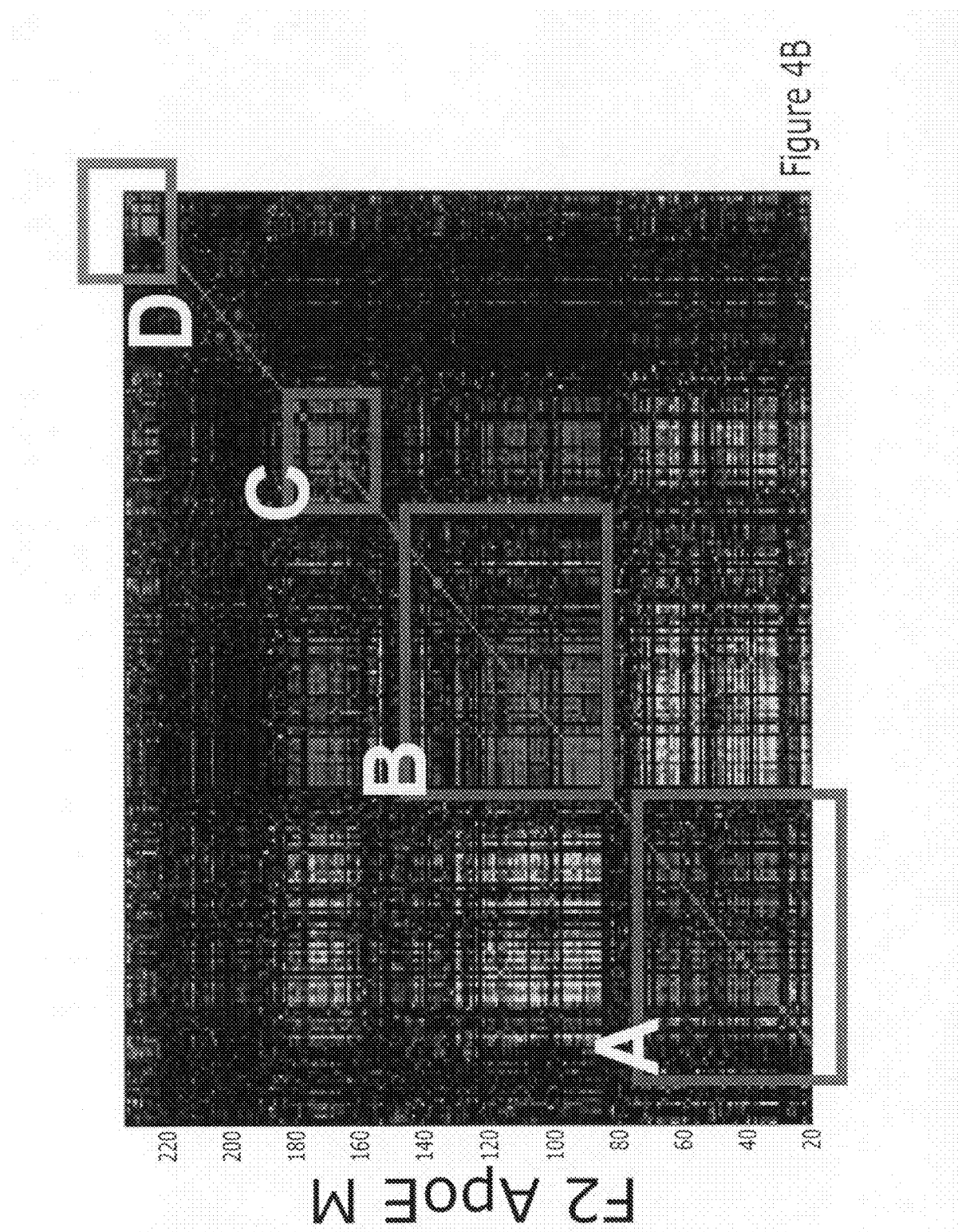
FIG. 4B illustrates a dataset after application of clustering methods in accordance with an embodiment of the present invention.
Figure 4C:
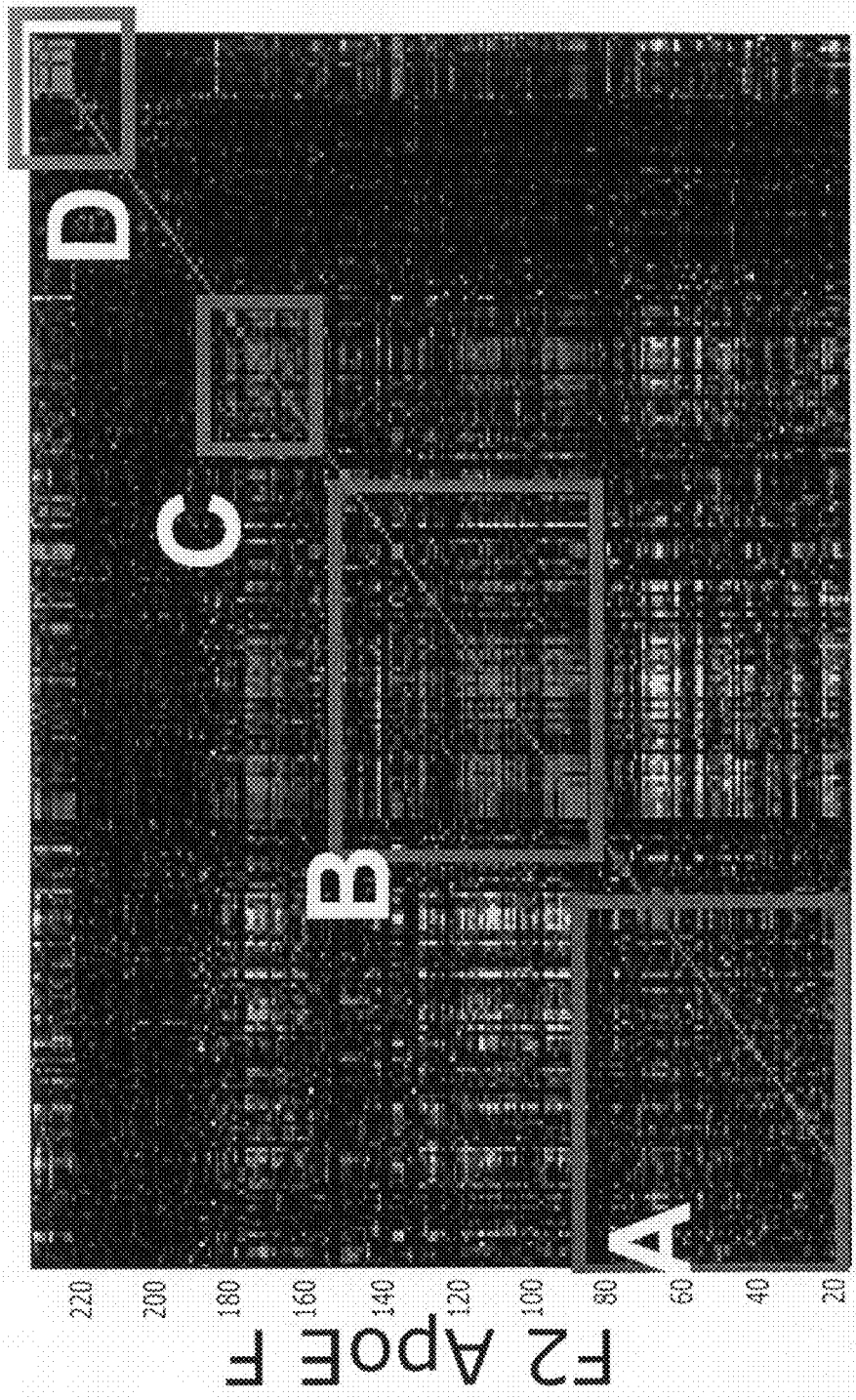
FIG. 4C illustrates a dataset after application of clustering methods in accordance with an embodiment of the present invention.
Figure 4D:
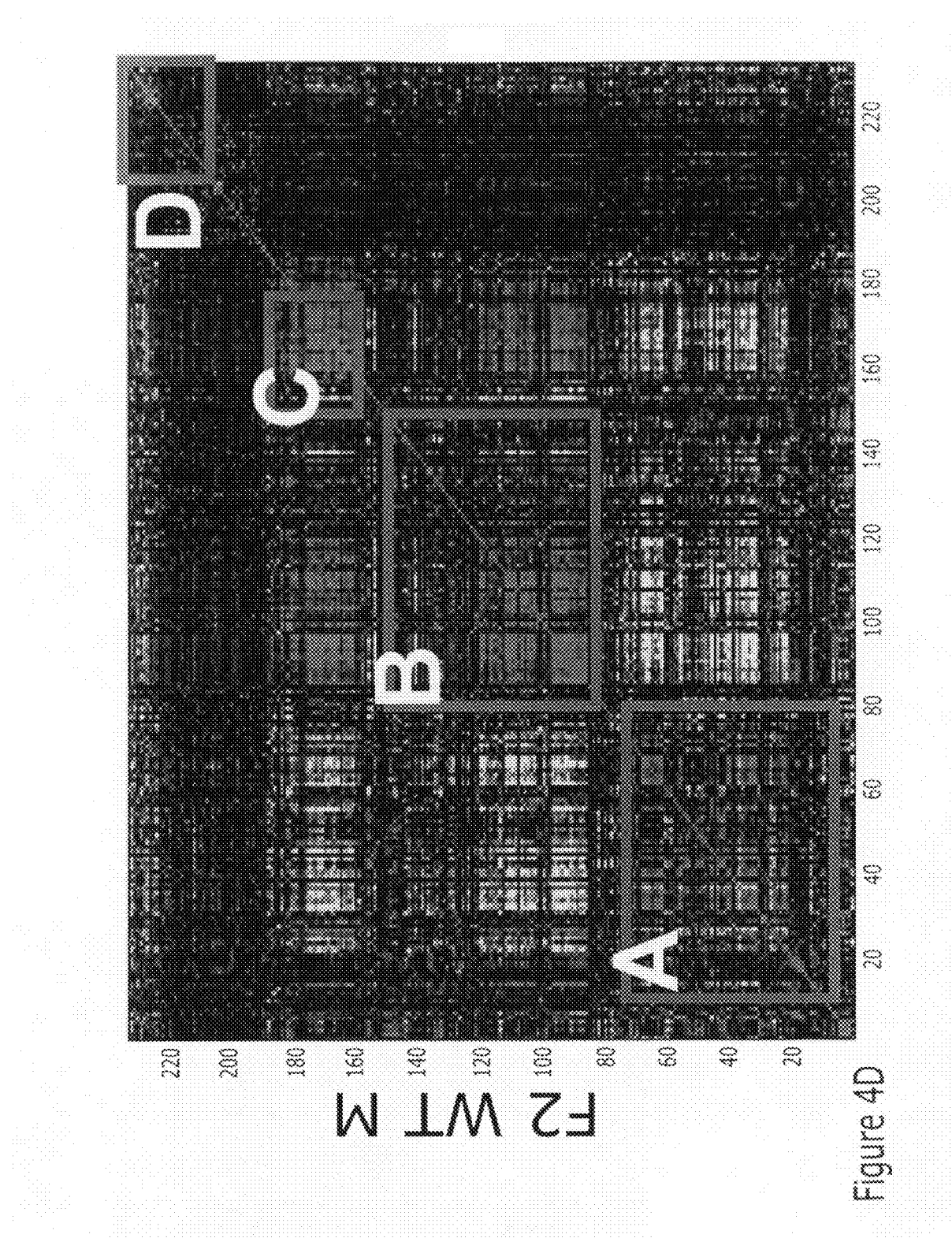
FIG. 4D illustrates a dataset after application of clustering methods in accordance with an embodiment of the present invention.
Figure 4E:
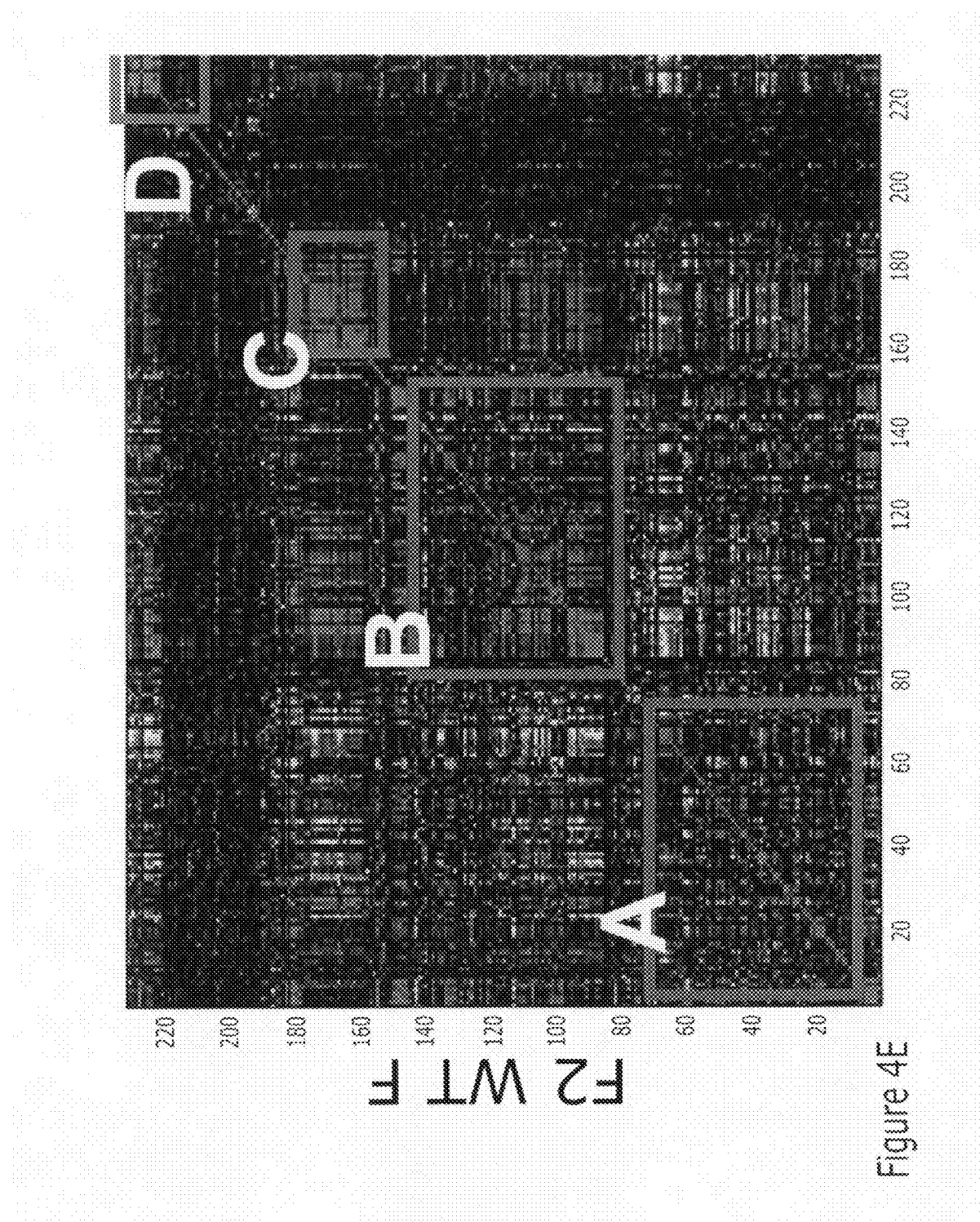
FIG. 4E illustrates a dataset after application of clustering methods in accordance with an embodiment of the present invention.

Two-dimensional grid maps were constructed for the remaining four datasets. The gene order obtained by clustering the MegaEG dataset was then applied to the other four two-dimensional grid maps so that any patterns of conservation could be easily observed. Four F2 crosses were included in the study: F2 WT F (C57B/6×C3H ApoE wildtype female F2), F2 WT M (C57B/6×C3H ApoE wildtype male F2), F2 ApoE F (C57B/6×C3H ApoE null female F2) and F2 ApoE M (C57B/6×C3H ApoE null male F2). FIG. 4B illustrates the two-dimensional correlation grid map for F2 ApoE M. FIG. 4C illustrates the two-dimensional correlation grid map for F2 ApoE F. FIG. 4D illustrates the two-dimensional correlation grid map for F2 WT M. FIG. 4D illustrates the two-dimensional correlation grid map for F2 WT F. Conserved clusters can be easily visualized across the five datasets, as blocks or modules along the diagonal in the color matrix display in FIGS. 4A and 4B through 4E.

In order to assess whether these clusters could have arisen by chance, 1000 Monte Carlo simulations were performed by permuting the gene expression vectors for each gene in the network. A threshold was set for the correlation coefficients from the permuted dataset in accordance with the thresholds used in the experimental datasets for identifying conserved clusters (e.g., absolute value of the correlation was set to be greater than 0.3). The P-value that the significant correlations occurred by chance was empirically estimated to be less than $10^{-4}$. The calculated P-value was a very conservative P-value done to get a rough estimate of the significance. It was estimated that the true P-value would be significantly smaller. Therefore, the conserved clusters unlikely arose by chance.

6.5. Identifying Conserved Clusters Across Different Datasets

Figure 5:
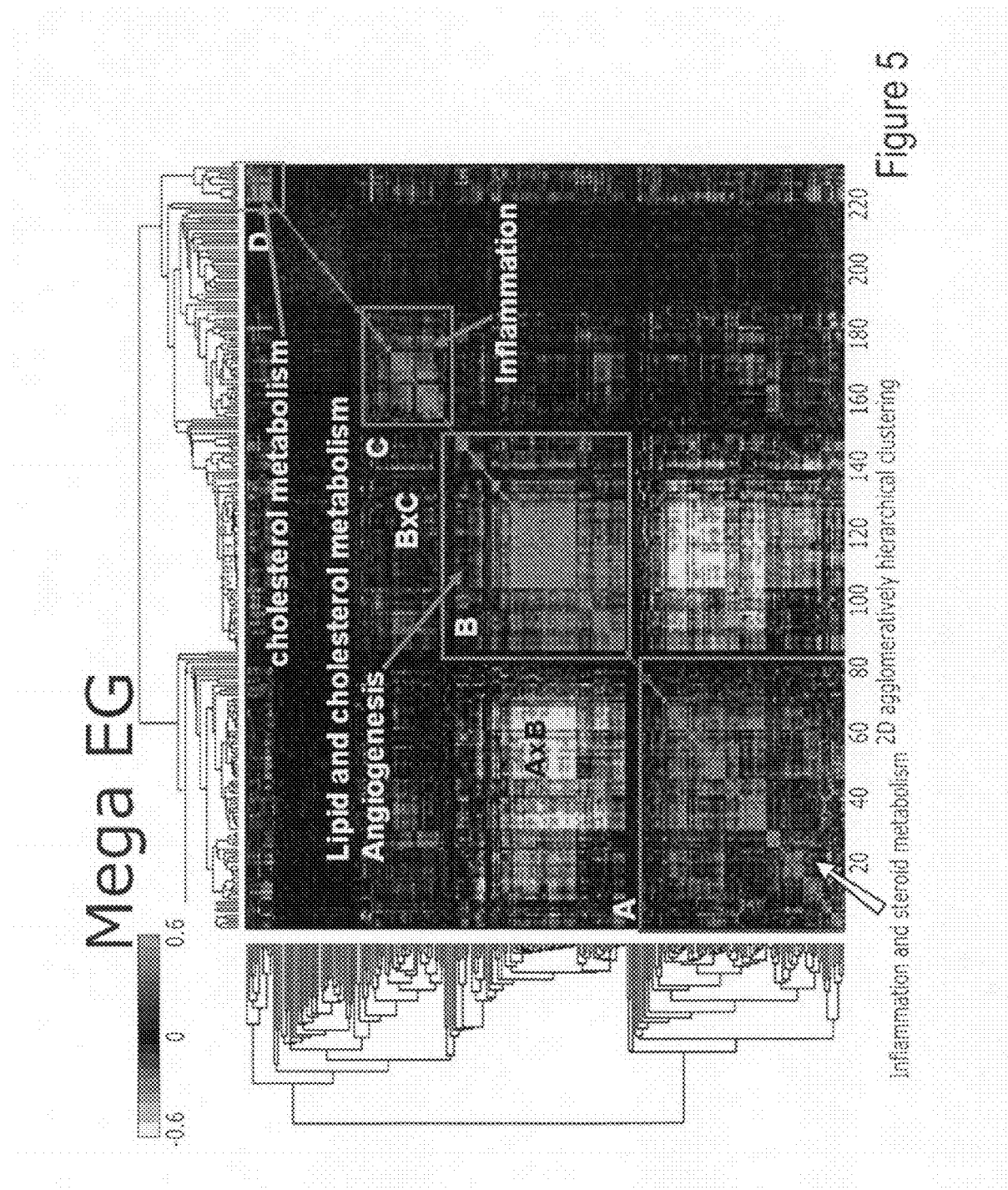
FIG. 5 illustrates a close-up view of FIG. 4A where genes in the conserved clusters are identified in accordance with an embodiment of the present invention.

The two-dimensional correlation grid maps at FIGS. 4A through 4E revealed four main clusters (A-D) that appeared to be conserved among the five different datasets. In addition, genes in these clusters were not only highly correlated among themselves but were also highly correlated with different clusters, especially in the case of clusters A and B (FIGS. 4 and 5), which highlights the interactions that likely exist among the highly connected clusters in the transcriptional networks (expected in networks with scale free properties). Upon closer examination, each cluster is shown to be enriched with genes of different biological pathways using the GO Biological Process categories definition. For example, cluster A was significantly enriched with genes related to inflammation and steroid metabolism (P-value$\leq 10^{-5}$), cluster B with genes in lipid, sterol metabolism and angiogenesis (P-value$\leq 10^{-3}$), cluster C with genes related to inflammation (P-value$\leq 10^{-10}$) and cluster D with genes related to sterol metabolism (P-value$\leq 10^{-9}$), as depicted in FIG. 5.

Genes involved in lipid metabolism as well as inflammation were known to be key in co-regulating lipid metabolism. For example, cluster D consists mainly of sterol biosynthesis genes that include HMG-CoA reductase, squalene epoxidase, Insig1, Cyp51, and Fdps. The key role of genes such as HMG-CoA reductase in the cholesterol biosynthesis pathway has already been confirmed. Interestingly, this cluster also contains a very novel gene, GPR91 that was recently found to be a possible receptor for succinate and may affect blood pressure (He et al., 2004, Nature 429, 188-93 and Wittenberger et al., 2001, J Mol Biol 307, 799-813, each of which is hereby incorporated by reference herein in its entirety). The cardiovascular franchise is pursuing GPR91 as a putative target for hypertension. Mouse liver genetics data also showed that GPR91 has putative causal linkages to insulin and fat mass related traits. Because GPR91 occurs in the same conserved co-expression hub as well studied cholesterol biosynthesis genes in the liver, these data indicate other possible roles for this recently de-orphanized GPCR in metabolic-related activities. The core of the cluster B genes was one of the most highly correlated clusters in the matrix. Among the genes in cluster B were Pdk4, Hao3, Lpl, Pla2g7 and Mgat1. Again, Hao3 was recently identified as causal for various metabolic traits in the F2 crosses, as well as being a down regulated gene in niacin treatment, making it a very attractive novel putative target. The tight association of Hao3 with other hub genes may also elucidate their activities in the liver.

6.6. Validating Conserved Gene-Gene Interactions in the Conserved Clusters

An experiment was performed in order to further understand the importance of the genes comprising the conserved clusters. Over 1200 liver gene expression traits, which were identified in any one of the three F2 mouse crosses (BxD, BxH/apoE, and BxH/wt) as causal for one or more metabolic trait (such as LDL, HDL, FFA and others), were intersected with the 233 genes identified from this study to identify the overlapping genes. Among the liver causal genes, 81 overlapped with the 233 genes in our conserved network. As determined by Fisher exact test, the P-value for the significance of this overlap happening by chance is less than $3.2 \times 10^{-39}$.

Figure 6:
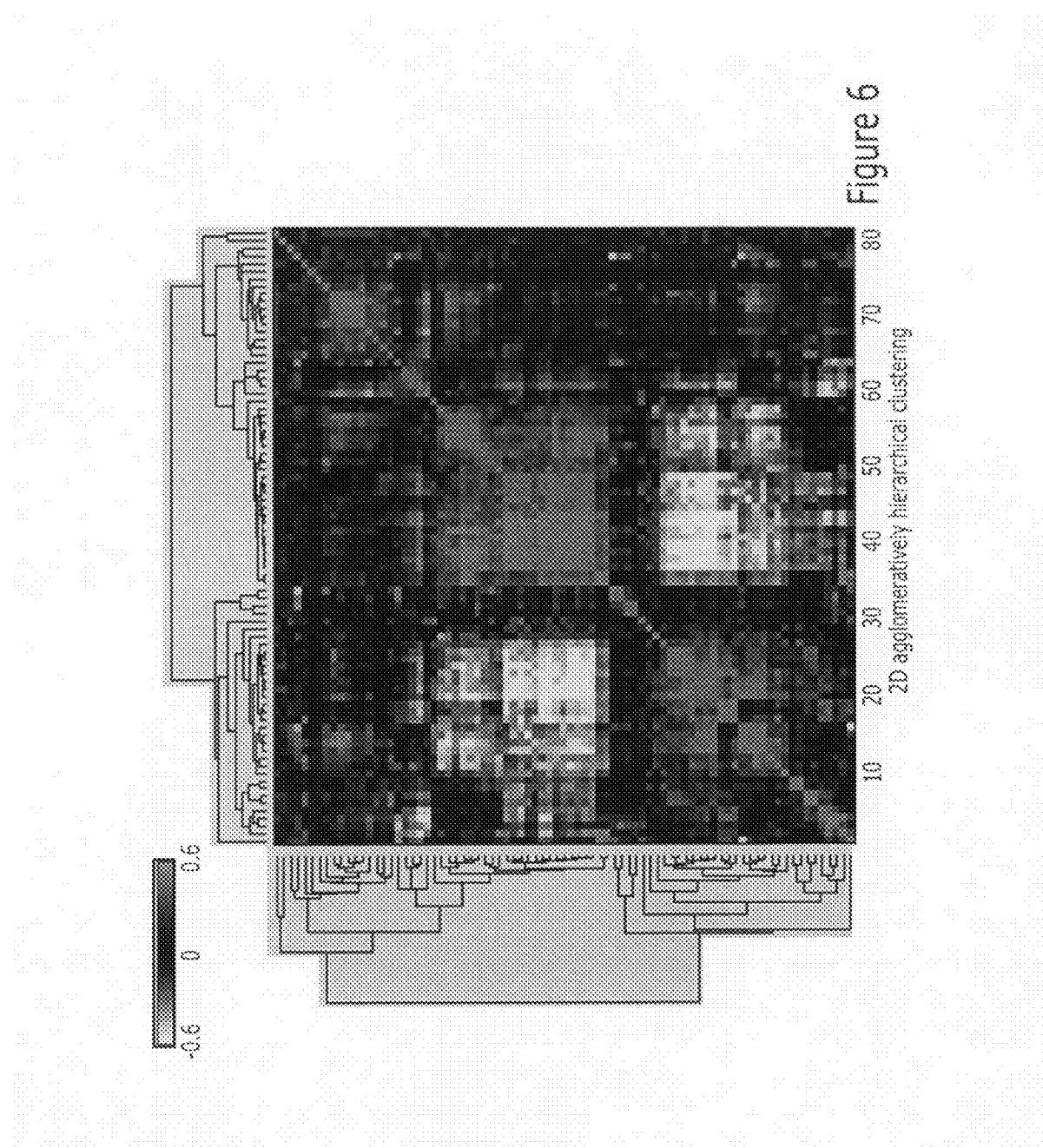
FIG. 6 illustrates a two-dimensional agglomerative clustering pattern of 81 causal genes from mouse liver causality test, in accordance with an embodiment of the present invention.

To better understand which components of the blocks shown in FIGS. 2 and 3 correspond to the liver causal genes, the 81 causal genes were also clustered. The result shown in FIG. 6 clearly demonstrates that the clustering pattern of the causal genes were similar to those of the randomly selected 233 genes. FIGS. 4A and B show that the hubs of highly correlated genes have the highest population of the causal genes that were included in FIG. 6. Many causal genes of high interest (i.e., many of the key drivers of disease we have identified) were identified in these conserved co-expression networks, making it easier to assign biological plausibility to them or to even prioritize them. Mgat1, Hao3, GPR91 are among the more novel causal genes that are in this matrix.

6.7. Gene-Gene Correlation Analysis for Human Tumor Tissues

Gene-gene correlation analysis as disclosed in this invention was also performed for gene expression data from human diseased tissues. Three datasets were constructed and used in the study: NKI(tumor), TA(tumor) and TA(normal). The NKI (tumor) dataset were generated from breast tumor tissues from 321 breast tumor patients in the Netherlands. The NKI (tumor) dataset was constructed at Netherlands Cancer Institute. The DNA microarray hybridization was carried out by the Kirkland facility at Rosetta Inpharmatics (Kirkland, Wash., United States). Details of the dataset and the relevant study can be found in "A Gene-Expression Signature as a Predictor of Survival in Breast Cancer" by Van de Vijver, et al., 2002, *New England Journal of Medicine* 347: 1999-2009 and "Gene Expression Profiling Predicts Clinical Outcome of Breast Cancer" by Van't Veer et al., 2002, *Nature* 415: 530-536; each of which is hereby incorporated by reference herein in its entirety.

The two TA datasets were generated in the United States. The samples used for the TA datasets were purchased from Collaborative Genomics, Inc. (Cambridge, Mass.), which was subsequently purchased by SeraCare Life Sciences, Inc. (West Bridgewater, Mass.). The TA(tumor) dataset included five different types of tumor samples, including breast, colon, gastric, kidney, and lung cancer samples. For each type of tumor, tumor samples and adjacent non-tumor samples were collected from 75 patients. The TA(normal) dataset included adjacent non-tumor (normal) samples from the same patients. Multiple samples were collected from the same patient. A total of 750 samples, consisting of 375 sample pairs, were collected. The samples were homogenized and divided into separate tubes for RNA and DNA extraction, respectively. RNA extractions were performed at Rosetta using standard conditions as described in the present application. DNA microarray hybridizations were carried out on Rosetta human 3 arrays (Human 3.0 A1) on Agilent 25K microarray from Agilent Life Sciences and Chemical Analysis (Santa Clara, Calif.). Details of the Human 3.0 A1 DNA array can be found in the Genomic Expression Omnibus (GEO) database hosted at the National Center for Biotechnology Information (NCBI) under the accession number GPL3991.

Unmatched samples and other samples that failed to achieve certain standards such as poor RNA quality, low RNA yield, and failure during RNA amplification, etc. were rejected in further analysis. Overall, 314 sample pairs were successfully profiled into the TA(tumor) and TA(normal)

datasets. For each tumor type, a pool of adjacent normal samples was created and used as the control sample for hybridizations against all tumor or normal samples. A total of 314 matched pair samples were successfully profiled in the TA datasets, including 59 breast cancer sample pairs, 65 colon cancer sample pairs, 71 gastric cancer sample pairs, 54 kidney cancer sample pairs, and 65 lung cancer sample pairs. Gene expression levels of approximately 12,000 genes were subject to unsupervised hierarchical agglomerative clustering analysis across an ordered list of the 314 sample pairs. In general, the samples within a tumor type gave patterns of expression more similar than the other tumor type samples, and the adjacent non-involved samples typically showed very few differentially expressed genes.

Figure 7:
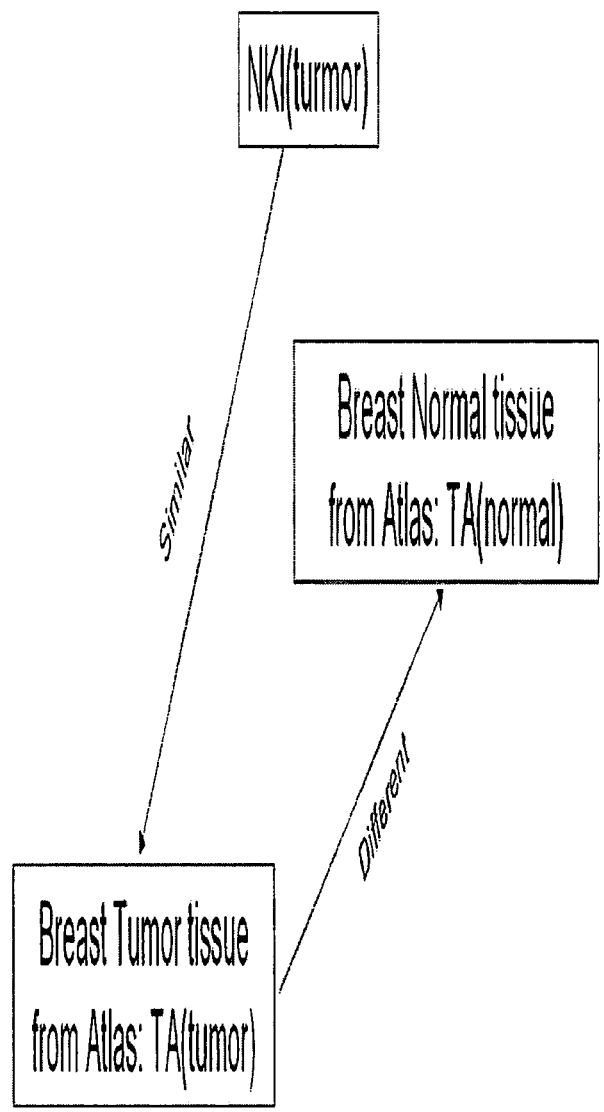
FIG. 7 illustrates an experimental set up for human breast cancer tissues, in accordance with an embodiment of the present invention.

The NKI and TA datasets were obtained in different laboratories, under different conditions and from independent patients that had different disease history and clinical parameters. As depicted in FIG. 7, the goal of this data analysis was to look at the synergy between the gene expression in the tumors of the NKI(tumor) and TA(tumor) datasets and then contrast it with the gene expression data in the normal tissue from the TA(normal) dataset. Since these data sets span completely different patients, under different experimental conditions the direct comparison of the patterns of expression was impossible between NKI and TA datasets. Gene-gene correlations were computed by the genepairs within the datasets to account for the consistent covariance properties between the genes.

Within each of the three datasets constructed, e.g., NKI (tumor), TA(tumor) and TA(normal), standard deviation of each gene was computed across different patients within each dataset. For example, the gene expression levels for a specific gene (e.g., gene #1) were quantified in all 321 patients in NKI(tumor). A standard deviation was then calculated for all the abundance data for gene #1, as summarized in step 208. The process was then repeated for every gene that was included in NKI dataset as well as for every gene that was included in TA(tumor) and TA(normal) datasets, as depicted in step 210. The standard deviations of all genes in each dataset were used to compute a median value of the standard deviation for the specific dataset (e.g., steps 214 and 216). A value of 0.2 was selected because it was larger than the median standard deviation of each dataset. The standard deviation of each gene from NKI dataset is compared to 0.2. If the standard deviation of a gene is smaller than 0.2, the gene will be rejected from the dataset. The process is repeated for TA(tumor) and TA(normal) datasets, rejecting all genes with a standard deviation smaller than 0.2, as depicted in steps 218 and 220. Among the remaining genes, 664 genes were found to be commonly present in all three datasets.

According to processes summarized in steps 230 through 238, correlation data for each gene pair of the 664 genes were first computed based on methods such as correlation coefficients. Subsequently, the correlation data for the TA(tumor) dataset was then clustered, using method such as 2D agglomerative clustering, as depicted in step 236. An order of the genes was defined such that it corresponds to the optimal clustering pattern for the TA(tumor) dataset. The obtained order of the genes was then projected onto the NKI(tumor) and TA(normal) datasets.

Figure 8:
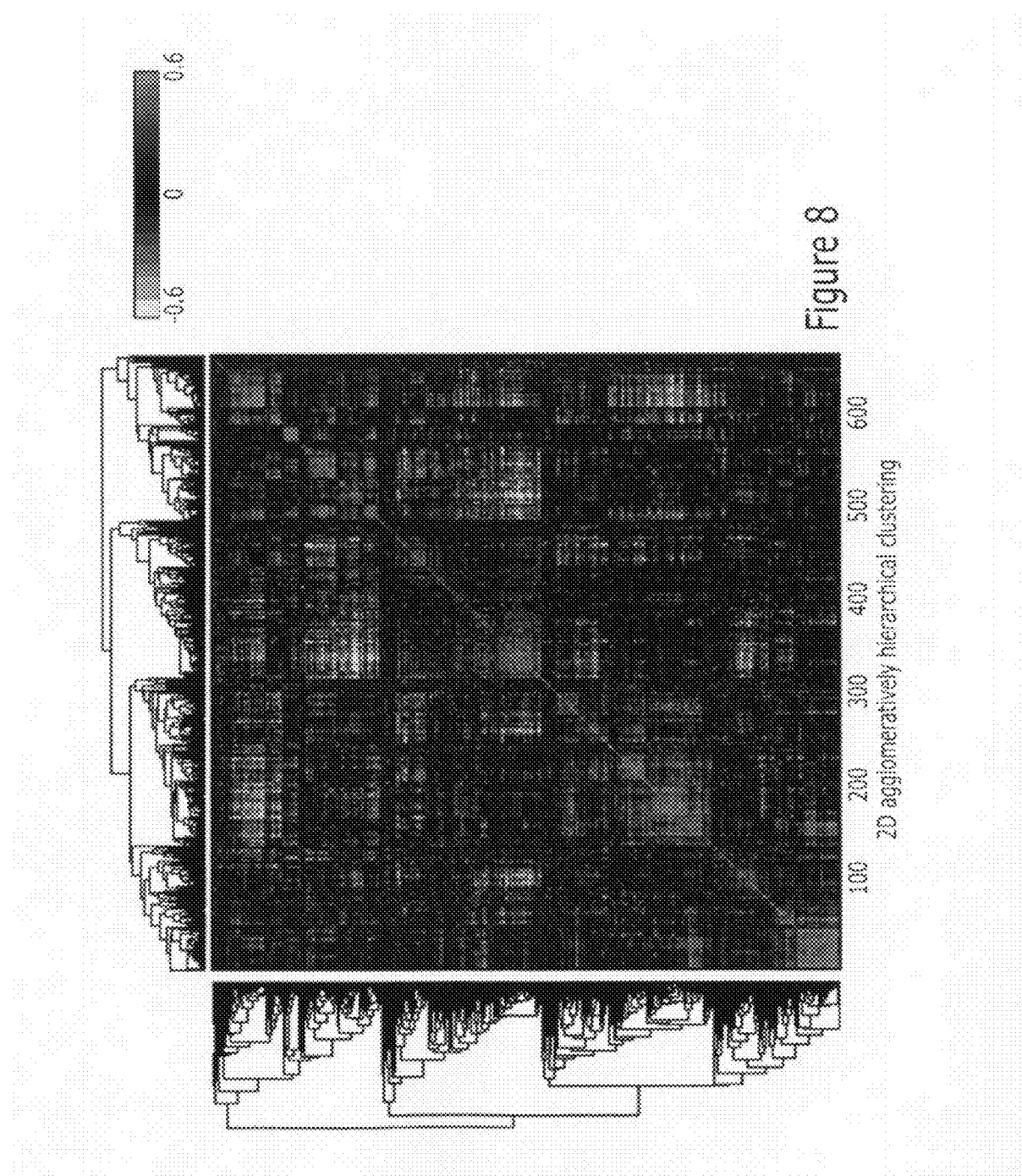
FIG. 8 illustrates a dataset after application of clustering methods in accordance with an embodiment of the present invention.

FIG. 8 illustrates the result after clustering analysis of the TA(tumor) dataset. The results revealed similar clustering patterns of correlations between the two tumor datasets. The results also revealed difference between the tumor datasets and the normal tissue dataset. Examining of the conserved clusters in the two tumor datasets and contrasting them with the clustering pattern for the normal tissue dataset reveal genes that may reflect on the cancer biology and serve as new drug targets.

6.8. Conclusions

In the example section, the existence of conserved gene-gene interaction networks in a diverse set of large-scale mouse liver gene expression experiments has been demonstrated. It also showed that the BxH/apoE and BxH/wt liver gene expression data represent networks between the genders and between the crosses that are also highly conserved. These networks are very significantly enriched with genes that were identified as causal for various metabolic traits and hence, are likely important for liver metabolism and related functions. The fact that these conserved networks have been obtained from two independent F2 crosses and a diversity of other liver experiments (e.g., drug treatments) further signifies their importance in liver biology.

Although gene-gene interaction networks only show functional relationships between gene pairs, the causality genes may be integrated into the analysis to refine the interpretation of these networks even further. The results suggest that systems and methods in accordance with the present invention are effective and efficient in identifying the most conserved gene-gene interaction networks. The results further suggest that the conserved co-expression networks may also serve as the initial building blocks for Bayesian network reconstruction processes, to refine gene-gene functional relationships and to assign directionality to the conserved gene-gene interactions. Even though the systems and methods were only applied to large scale of mouse liver experiments, they sufficed to provide the most strongly conserved components of the transcriptional network in the single tissue. They further demonstrate that the novel approach in accordance with the present invention to elucidating interaction networks has the potential to help us focus on prioritizing new targets and assigning biological relevance to novel and interesting potential drug targets. Breast cancer tissue analyses further demonstrate that the methods and systems disclosed in the present invention are applicable to human tissues. Furthermore, methods and systems disclosed in the present invention are helpful in illustrating differences between normal tissues and tissues in diseased states.

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed:

1. A method of determining whether there is a functional relationship between a first cellular constituent and a second cellular constituent, the method comprising:
   (a) in a computer system, generating a first cellular constituent correlation matrix of a first plurality of correlation coefficients, wherein respective correlation coefficients in said first plurality of correlation coefficients represent a correlation between first cellular constituent abundance measurement data for a pair of cellular constituents from a plurality of organisms subject to a same experimental condition, the respective correlation coefficients in said first plurality of correlation coefficients being computed for a different pair of cellular constituents, wherein the cellular constituents in the first plurality of cellular constituents are selected from a plurality of cellular constituents based on a threshold increase in variance calculated by comparing the variance of the cellular abundance measurement data for a cellular constituent from the plurality of organisms subject to the same experimental condition with the variance of cellular abundance measurement data for a plurality of cellular constituents in the respective plurality of organisms subject to the same experimental condition, wherein said generating of the first cellular constituent correlation matrix is according to a preselected order of cellular constituents in the pairs of cellular constituents for which said first plurality of correlation coefficients is computed, wherein said preselected order of cellular constituents in the pairs of cellular constituents for which said first plurality of correlation coefficients is computed is determined by clustering said first plurality of correlation coefficients, and each said pair of cellular constituents comprising a first cellular constituent and a second cellular constituent;

(b) in the computer system, applying the preselected order to generate a second cellular constituent correlation matrix of a second plurality of correlation coefficients, wherein each correlation coefficient in said second plurality of correlation coefficients represents a correlation between second cellular constituent abundance measurement data for said pairs of cellular constituents for which said first plurality of correlation coefficients is computed, and said second cellular constituent abundance measurement data being from each of a plurality of organisms subject to a second experimental condition, said second experimental condition differing from said first experimental condition;

(c) optionally repeating step (b) one or more times, each time generating a different cellular constituent correlation matrix of a different plurality of correlation coefficients thereby forming a plurality of cellular constituent correlation matrices, wherein the respective different plurality of correlation coefficients is computed using cellular constituent abundance measurement data from a plurality of organisms, each plurality of organisms being subject to different respective experimental conditions; and wherein when a conserved area among said plurality of cellular constituent correlation matrices is present, a functional relationship between said first cellular constituent and said second constituent is determined to be present; and when a conserved area among said plurality of cellular constituent correlation matrices is not present, a functional relationship between said first cellular constituent and said second constituent is not determined to be present; and (d) outputting to a user interface device, a computer readable storage medium, or a local or remote computer system; or displaying; the cellular constituent correlation matrices, or an indication of whether a functional relationship is determined to be present between said first cellular constituent and said second cellular constituent.

2. The method of claim 1, wherein said first, second and different cellular constituent correlation matrices are two-dimensional, and the preselected order is the same along each axis of the first, second and different cellular constituent correlation matrices.

3. The method of claim 1 which further comprises a step of computing said first, second and different pluralities of correlation coefficients.

4. The method of claim 1, further comprising:
assigning a visible color signal to the correlation coefficients, such that the nature of color reflects the value of the correlation coefficient.

5. A method of determining whether there is a functional relationship between a first cellular constituent and a second cellular constituent, the method comprising:

(a) receiving a plurality of datasets, wherein
the respective datasets in said plurality of datasets comprise cellular constituent abundance measurement data for a plurality of cellular constituents from a plurality of organisms subject to an experimental condition, wherein the respective datasets are from organisms subject to different experimental conditions, and wherein the respective datasets comprise cellular constituent abundance measurement data for said plurality of cellular constituents;

wherein the cellular constituents in the plurality of cellular constituents are selected from a plurality of cellular constituents based on a threshold increase in variance calculated by comparing the variance of the cellular abundance measurement data for a cellular constituent from the plurality of organisms subject to the experimental condition with the variance of cellular abundance measurement data for a plurality of cellular constituents in the respective plurality of organisms subject to the experimental condition, (b) in a computer system, computing a plurality of correlation coefficients for the respective datasets in said plurality of datasets, wherein the correlation coefficient in said plurality of correlation coefficients for a respective dataset in said plurality of datasets represents a correlation between cellular constituent abundance measurement data for a pair of cellular constituents in said plurality of cellular constituents across the plurality of organisms of the respective dataset, said pair of cellular constituents comprising a first cellular constituent and a second cellular constituent, and the correlation coefficient in said plurality of correlation coefficients being computed for a different pair of cellular constituents;

(c) in the computer system, applying a preselected order of said plurality of cellular constituents to the plurality of correlation coefficients of the respective datasets in said plurality of datasets, wherein said preselected order of said plurality of cellular constituents is determined by clustering said plurality of correlation coefficients of a dataset in said plurality of datasets, thereby forming a plurality of cellular constituent correlation matrices; wherein when a conserved area among said plurality of cellular constituent correlation matrices that comprises said first cellular constituent and said second cellular constituent is present, said functional relationship between said first cellular constituent and said second constituent is determined to be present; and when a conserved area among said plurality of cellular constituent correlation matrices that comprises said first cellular constituent and said second cellular constituent is not present, said functional relationship between said first cellular constituent and said second constituent is not determined to be present; and (d) outputting to a user interface device, a computer readable storage medium, or a local or remote computer system; or displaying; the cellular constituent correlation matrices, or an indication of whether a functional relationship is determined to be present between said first cellular constituent and said second cellular constituent.

6. A computer program product not consisting of a signal and comprising a computer readable storage medium and an executable computer program mechanism embedded therein, the executable computer program mechanism causing a computer system to perform a method of determining a functional relationship between a first cellular constituent and a second cellular constituent, the method comprising:

(a) generating a first cellular constituent correlation matrix of a first plurality of correlation coefficients, wherein respective correlation coefficients in said first plurality of correlation coefficients represent a correlation between first cellular constituent abundance measurement data for a pair of cellular constituents from a plurality of organisms subject to a same experimental condition, the respective correlation coefficients in said first plurality of correlation coefficients being computed for a different pair of cellular constituents, wherein the cellular constituents in the first plurality of cellular constituents are selected from a plurality of cellular constituents based on a threshold increase in variance calculated by comparing the variance of the cellular abundance measurement data for a cellular constituent from the plurality of organisms subject to the same experimental condition with the variance of cellular abundance measurement data for a plurality of cellular constituents in the respective plurality of organisms subject to the same experimental condition, wherein said generating of the first cellular constituent correlation matrix is according to a preselected order of cellular constituents in the pairs of cellular constituents for which said first plurality of correlation coefficients is computed, wherein said preselected order of cellular constituents in the pairs of cellular constituents for which said first plurality of correlation coefficients is computed is determined by clustering said first plurality of correlation coefficients, and each said pair of cellular constituents comprising a first cellular constituent and a second cellular constituent;

(b) applying the preselected order to generate a second cellular constituent correlation matrix of a second plurality of correlation coefficients, wherein the respective correlation coefficients in said second plurality of correlation coefficients represents a correlation between second cellular constituent abundance measurement data for said pairs of cellular constituents for which said first plurality of correlation coefficients is computed, and said second cellular constituent abundance measurement data being from a plurality of organisms subject to a second experimental condition, said second experimental condition differing from said first experimental condition;

(c) optionally repeating step (b) one or more times, each time generating a different cellular constituent correlation matrix of a different plurality of correlation coefficients thereby forming a plurality of cellular constituent correlation matrices, wherein the respective different plurality of correlation coefficients is computed using cellular constituent abundance measurement data from a plurality of organisms, the plurality of organisms being subject to different respective experimental conditions; and wherein when a conserved area among said plurality of cellular constituent correlation matrices is present, a functional relationship between said first cellular constituent and said second constituent is determined to be present; and when a conserved area among said plurality of cellular constituent correlation matrices is not present, a functional relationship between said first cellular constituent and said second constituent is not determined to be present; and (d) outputting to a user interface device, a computer readable storage medium, or a local or remote computer system; or displaying; the cellular constituent correlation matrices, or an indication of whether a functional relationship is determined to be present between said first cellular constituent and said second cellular constituent.

7. The computer program product of claim 6, wherein the method further comprises:

instructions for assigning a visible color signal to the respective correlation coefficients, such that the nature of color reflects the value of the correlation coefficient.

8. A computer system for determining a functional relationship between a first cellular constituent and a second cellular constituent, the computer system comprising:

a central processing unit; and a memory, coupled to the central processing unit, the central processing unit processing computer-executable instructions stored in the memory, the computer-executable instructions causing the computer system to perform the following:

(a) generating a first cellular constituent correlation matrix of a first plurality of correlation coefficients, assigning a visible color signal to respective of the correlation coefficients, such that the nature of color reflects the value of the correlation coefficient, wherein the respective correlation coefficients in said first plurality of correlation coefficients represents a correlation between first cellular constituent abundance measurement data for a pair of cellular constituents from each of a plurality of organisms subject to a same experimental condition, the respective correlation coefficients in said first plurality of correlation coefficients being computed for a different pair of cellular constituents, wherein the first cellular constituent abundance measurement data is normalized using a Z-score of intensity, wherein the cellular constituents in the first plurality of cellular constituents are selected from a plurality of cellular constituents based on a threshold increase in variance calculated by comparing the variance of the cellular abundance measurement data for a cellular constituent from the plurality of organisms subject to the same experimental condition with the variance of cellular abundance measurement data for a plurality of cellular constituents in the respective plurality of organisms subject to the same experimental condition, wherein said generating of the first cellular constituent correlation matrix is according to a preselected order of cellular constituents in the pairs of cellular constituents for which said first plurality of correlation coefficients is computed, wherein said preselected order of cellular constituents in the pairs of cellular constituents for which said first plurality of correlation coefficients is computed is determined by clustering said first plurality of correlation coefficients, and each said pair of cellular constituents comprising a first cellular constituent and a second cellular constituent;

(b) applying the preselected order to generate a second cellular constituent correlation matrix of a second plurality of correlation coefficients, wherein respective correlation coefficients in said second plurality of correlation coefficients represent a correlation between second cellular constituent abundance measurement data for said pairs of cellular constituents for which said first plurality of correlation coefficients is computed, and said second cellular constituent abundance measurement data being from a plurality of organisms subject to a second experimental condition, said second experimental condition differing from said first experimental condition;

(c) optionally repeating step (b) one or more times, each time generating a different cellular constituent correlation matrix of a different plurality of correlation coefficients thereby forming a plurality of cellular constituent correlation matrices, wherein the respective different plurality of correlation coefficients is computed using cellular constituent abundance measurement data from a plurality of organisms, the respective plurality of organisms being subject to different respective experimental conditions; and wherein when a conserved area among said plurality of cellular constituent correlation matrices is present, a functional relationship between said first cellular constituent and said second constituent is determined to be present; and when a conserved area among said plurality of cellular constituent correlation matrices is not present, a functional relationship between said first cellular constituent and said second constituent is not determined to be present; and (d) outputting to a user interface device, a computer readable storage medium, or a local or remote computer system; or displaying; the cellular constituent correlation matrices, or an indication of whether a functional relationship is determined to be present between said first cellular constituent and said second cellular constituent.

* * * * *